US011328823B2

(12) United States Patent
Goldstein

(10) Patent No.: US 11,328,823 B2
(45) Date of Patent: May 10, 2022

(54) WEARABLE DEVICE FOR REDUCING EXPOSURE TO PATHOGENS OF POSSIBLE CONTAGION

(71) Applicant: Steven W. Goldstein, Delray Beach, FL (US)

(72) Inventor: Steven W. Goldstein, Delray Beach, FL (US)

( * ) Notice: Subject to any disclaimer, the term of this patent is extended or adjusted under 35 U.S.C. 154(b) by 0 days.

(21) Appl. No.: 16/949,088

(22) Filed: Oct. 13, 2020

(65) Prior Publication Data

US 2022/0115137 A1 Apr. 14, 2022

(51) Int. Cl.
| | | |
|---|---|---|
| *G16H 50/30* | (2018.01) | |
| *A61B 5/00* | (2006.01) | |
| *A61B 5/117* | (2016.01) | |
| *G16H 50/20* | (2018.01) | |
| *G06N 20/00* | (2019.01) | |
| *G16H 50/80* | (2018.01) | |

(52) U.S. Cl.
CPC ............ *G16H 50/30* (2018.01); *A61B 5/117* (2013.01); *A61B 5/6801* (2013.01); *A61B 5/742* (2013.01); *A61B 5/7455* (2013.01); *A61B 5/7475* (2013.01); *G06N 20/00* (2019.01); *G16H 50/20* (2018.01); *G16H 50/80* (2018.01)

(58) Field of Classification Search
CPC ..... A61B 5/6801; A61B 5/742; A61B 5/7455; A61B 5/7475; G06N 20/00; G16H 50/30; G16H 50/20; G16H 50/80
See application file for complete search history.

(56) References Cited

U.S. PATENT DOCUMENTS

| | | |
|---|---|---|
| 8,795,168 B2 | 8/2014 | Goh et al. |
| 9,196,139 B2 * | 11/2015 | Gutierrez ............... G08B 13/22 |
| 10,198,779 B2 | 2/2019 | Pittman et al. |
| 10,251,610 B2 | 4/2019 | Parthasarathy et al. |
| 10,303,843 B2 | 5/2019 | Bitran et al. |

(Continued)

OTHER PUBLICATIONS https://arxiv.org/pdf/2007.11147.pdf.
https://www.frontiersin.org/articles/10.3389/fdgth.2020.00008/full.
https://www.pipernetworks.com/vitrace/.

*Primary Examiner* — Lynsey C Eiseman
*Assistant Examiner* — Amanda L Steinberg
(74) *Attorney, Agent, or Firm* — Caldwell Intellectual Property Law, LLC

(57) ABSTRACT

A wearable device for reducing exposure to pathogens of possible contagion includes a detection component configured to detect a proximate subject in relation to a user wherein the user is in possession of the wearable device, a data input component configured to capture data relating to the proximate subject, wherein the data relating to the currently proximate subject further comprises an inoculation status of the currently proximate subject, a processor configured to calculate a degree of transmission threat between the user and the proximate subject, wherein calculating the degree of transmission threat further comprises identifying a pathogen of possible contagion, locating a reproduction rate for the pathogen of possible contagion, calculating the degree of transmission threat as a function of the data input component and the reproduction rate, and a user-signaling component configured to generate an output as a function of the degree of transmission threat.

18 Claims, 13 Drawing Sheets

(56) References Cited

U.S. PATENT DOCUMENTS

| | | |
|---|---|---|
| 10,664,572 B2 * | 5/2020 | Bitran .................... G16H 40/20 |
| 2008/0177574 A1 * | 7/2008 | Lara Gonzalez .... G08B 21/028 705/2 |
| 2016/0057565 A1 * | 2/2016 | Gold ....................... H04W 4/80 455/41.1 |
| 2016/0132652 A1 | 5/2016 | Chapman Bates et al. |
| 2017/0011131 A1 * | 1/2017 | Li ........................... G16H 50/80 |
| 2017/0019787 A1 * | 1/2017 | Castro .................. H04L 63/104 |
| 2017/0024531 A1 * | 1/2017 | Malaviya ............... G16H 40/63 |
| 2017/0091698 A1 * | 3/2017 | Holler .................... G06Q 10/00 |
| 2017/0206334 A1 | 7/2017 | Huang |
| 2018/0181714 A1 | 6/2018 | Pillarisetty et al. |
| 2019/0252078 A1 * | 8/2019 | Schubert ................ G16H 10/60 |
| 2020/0060556 A1 | 2/2020 | Olivero |
| 2020/0176125 A1 | 6/2020 | Chatterjea et al. |
| 2020/0242360 A1 * | 7/2020 | Alexander ............ G06T 19/006 |

\* cited by examiner

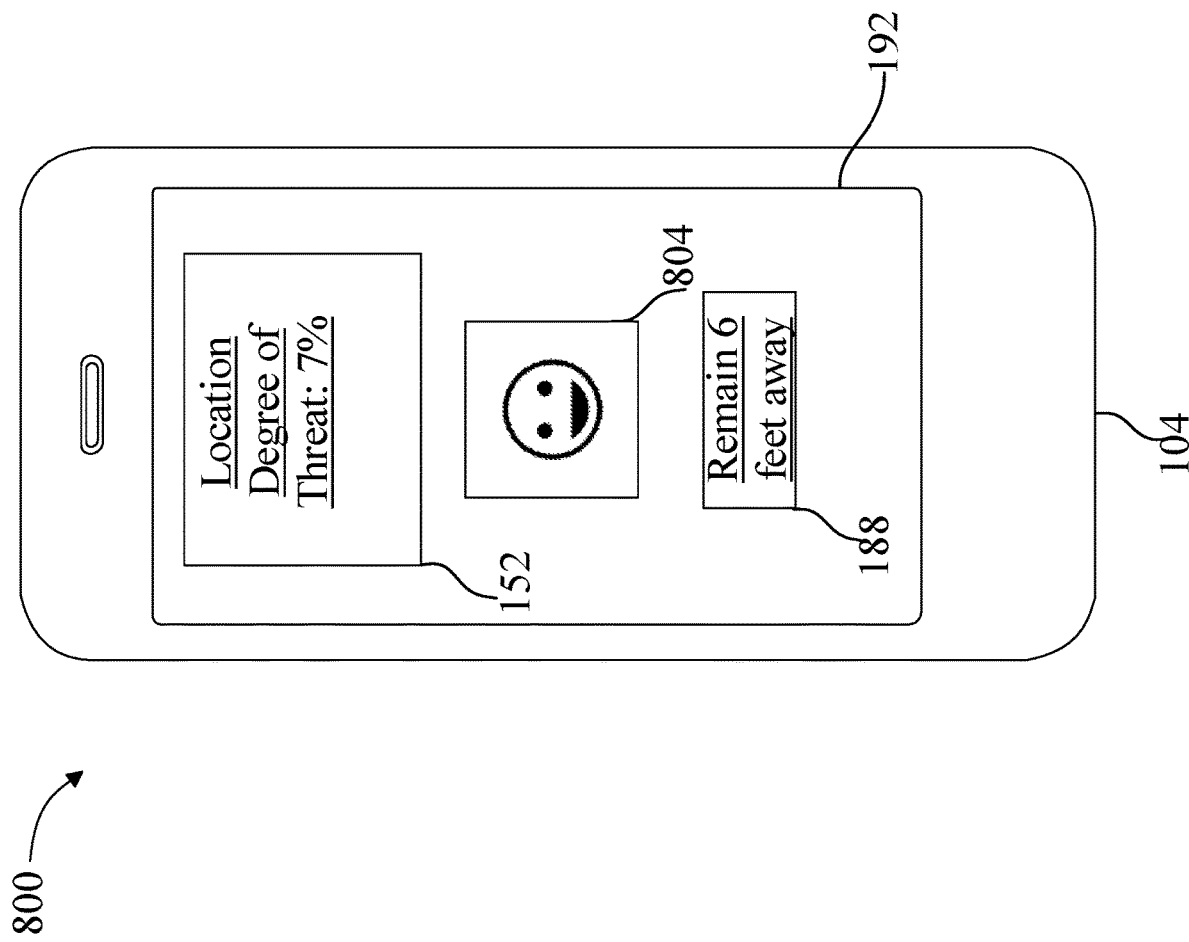

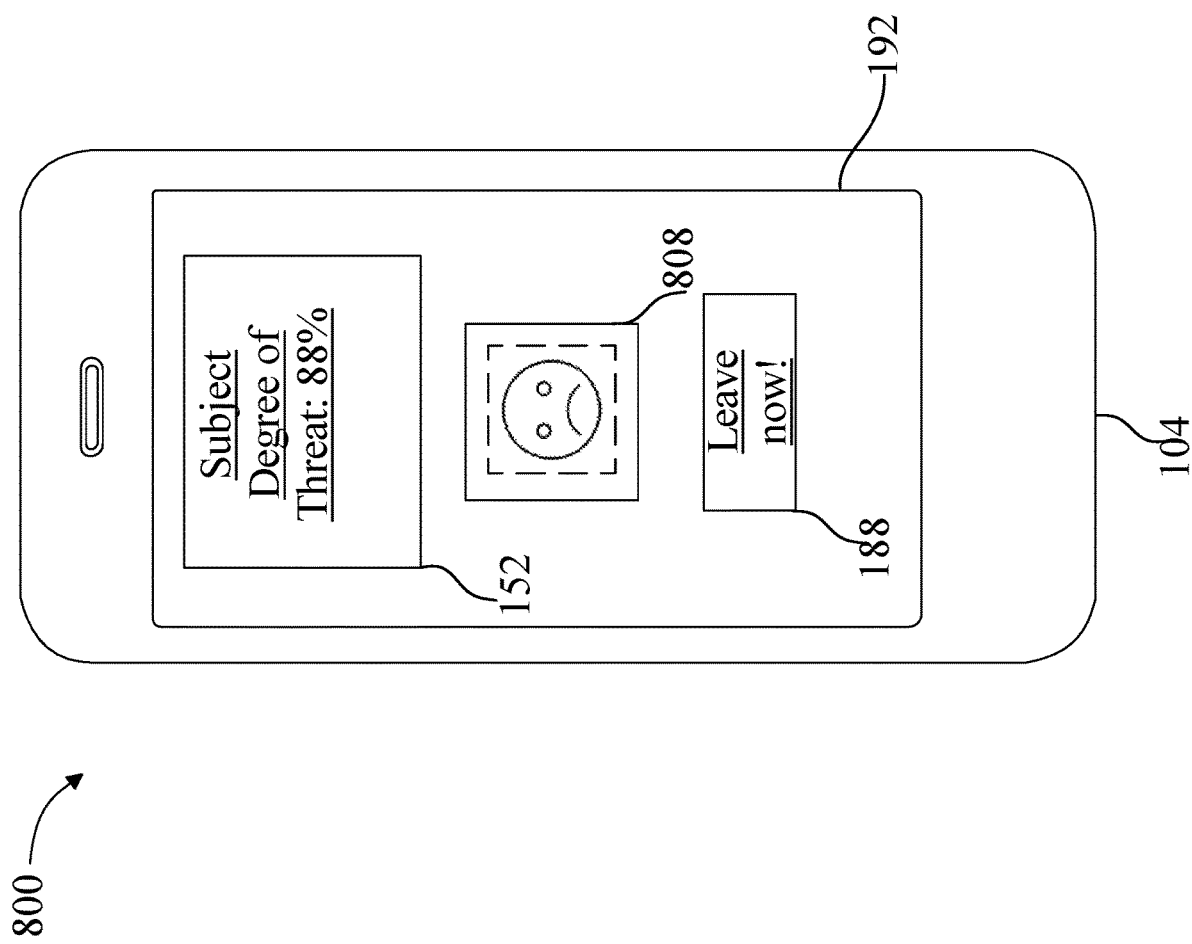

WEARABLE DEVICE FOR REDUCING EXPOSURE TO PATHOGENS OF POSSIBLE CONTAGION

FIELD OF THE INVENTION

The present invention generally relates to the field of infectious diseases. In particular, the present invention is directed to a wearable device for reducing exposure to pathogens of possible contagion.

BACKGROUND

Uncertainty surrounding safety of public spaces and shared locations can be challenging. Existing challenges fail to adequately provide reassurances surrounding interactions with strangers, locations, and/or vendors.

SUMMARY OF THE DISCLOSURE

In an aspect, a wearable device for reducing exposure to pathogens of possible contagion, the wearable device comprising a detection component configured to detect a currently proximate subject in relation to a user wherein the user is in possession of the wearable device, a data input component configured to capture data relating to the currently proximate subject, wherein the data relating to the currently proximate subject further comprises an inoculation status of the currently proximate subject, a processor configured to calculate a degree of transmission threat between the user and the currently proximate subject, wherein calculating the degree of transmission threat further comprises identifying a pathogen of possible contagion, locating a reproduction rate for the pathogen of possible contagion, and calculating the degree of transmission threat as a function of the data input component and the reproduction rate, and a user-signaling component configured to generate an output as a function of the degree of transmission threat.

In an aspect, a method of reducing exposure to pathogens of possible contagion the method comprising detecting by a wearable device, a currently proximate subject in relation to a user wherein the user is in possession of the wearable device; capturing by the wearable device, data relating to the currently proximate subject, wherein the data relating to the currently proximate subject further comprises an inoculation status of the currently proximate subject, calculating by the wearable device, a degree of transmission threat between the user and the currently proximate subject, wherein calculating the degree of transmission threat further comprises identifying a pathogen of possible contagion, locating a reproduction rate for the pathogen of possible contagion, and calculating the degree of transmission threat as a function of the data relating to the currently proximate subject and the reproduction rate, and generating by the wearable device, an output as a function of the degree of transmission threat.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 8A-C are diagrammatic representations of exemplary embodiments of signaling component;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments disclosed herein harness detection technology and opt-in protocols to identify relatively safe navigational routes and locations for users with regard to pathogen exposure. At a high level, aspects of the present disclosure are directed to a wearable device for reducing exposure to pathogens of possible contagion by determining localized data relating to infection rates and inoculation statuses. In an embodiment, a proximate subject is detected, and data is captured relating to the proximate subject. A degree of transmission threat is calculated by a wearable device by identifying a pathogen of possible contagion and locating a "localized" reproduction rate for the pathogen of possible contagion and the user's personal health profile. A user-signaling component generates an output as a function of a degree of transmission threat. An output may alert a user as to a potentially dangerous situation.

Figure 1:
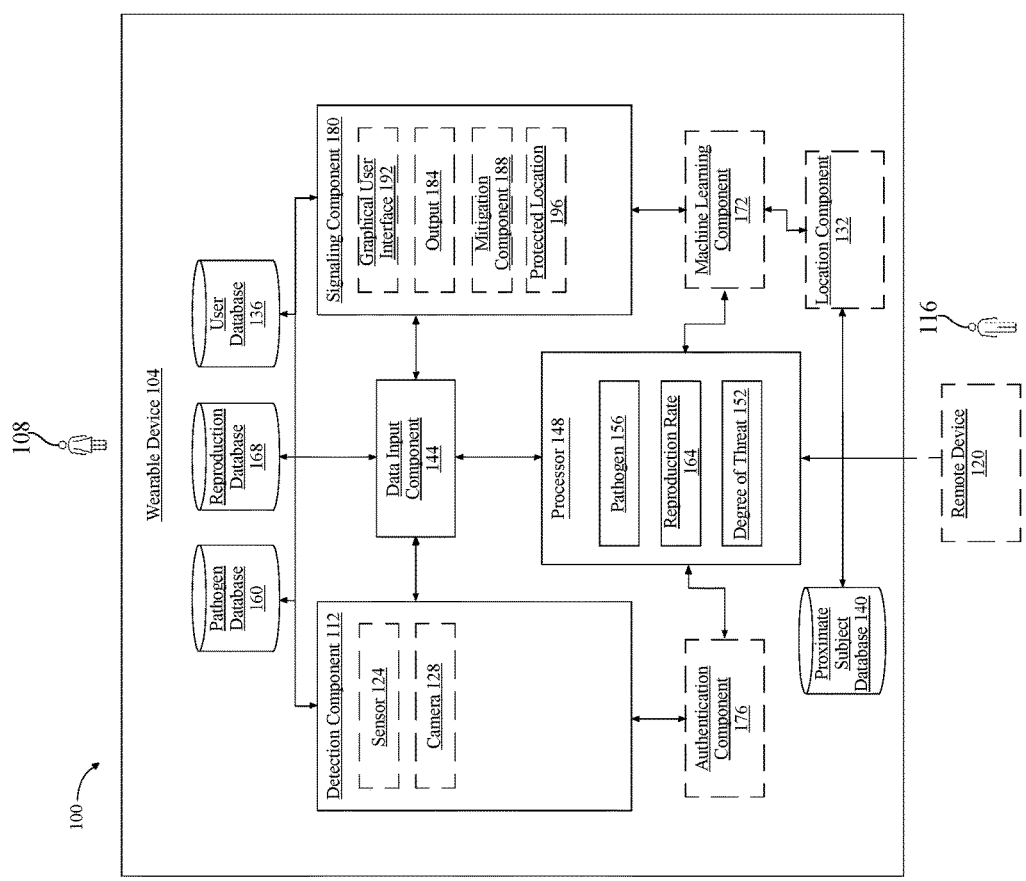
FIG. 1 is a block diagram illustrating an exemplary embodiment of a wearable device for reducing exposure to pathogens of possible contagion.

Referring now to the drawings, FIG. 1 illustrates an exemplary embodiment of a wearable device for reducing exposure to pathogens of possible contagion. A "wearable device," as used in this disclosure, is an electronic device that may be worn and/or to a user in close proximity or within visual and or audible range. A wearable device 104 may include an electronic device that may detect, analyze, and/or transmit information concerning a user, and may be configured to provide feedback for the user. Furthermore, the device may acquire information from the target site at an individual level as well as swarm level, in addition, the wearable device can calculate distances and proximity to other individuals as well a swarm or multiple swarms of individuals. A wearable device 104 may make contact and/or touch one or more body parts of a user, including but not limited to the fingers, palm, wrists, chest, forearms, ears, eyes, ear canal. forehead, temple, back, foot, ankle, and the like. In an embodiment, a wearable device 104 may not make contact and/or touch one or more body parts of a user, but rather may be in the vicinity and/or located adjacent to a user, such as a computer and/or mobile phone, as described below in more detail. A wearable device 104 may be worn as an accessory, embedded in clothing worn by a user, implanted on a user's body, and/or tattooed onto a user's skin. For instance and without limitation, a wearable device 104 may include a smartwatch, a fitness tracker, a sports watch, a head-mounted display, a virtual reality headset, smart glasses, hearables, smart jewelry, smart clothing, hearing aids, and the like. A wearable device 104 may include any electrical equipment controlled by a central processing unit (CPU) such as but not limited to a laptop computer, a desktop computer, a smartphone, a mobile device, a computerized medical device, a tablet, and the like. A wearable device 104, may be operated by a user 108. A wearable device 104 may include a service, such as but not limited to a software and/or hardware module. A wearable device 104 may include and/or interact with a cloud based and/or internet of things (IOT) based application, including but not limited to infrastructure as a service (IaaS), platform as a service (PaaS), software as a service (Saas), mobile backend as a service (MBaaS), serverless computing, function as a service (FaaS) and the like. In an embodiment, cloud based services may include but are not limited to a private cloud, a public cloud, a hybrid cloud, a community cloud, a multi-cloud, a poly cloud, a big data cloud, a high-performance computing (HPC) cloud and the like. This may include sensor networks located in commercial buildings, people count, airflow, temperature fluctuations, sanitation (bathrooms etc.), elevator occupancy and the like. This may include office and/or home appliances, thermostats, and/or humidistats. A "user," as used in this disclosure, is a human subject.

With continued reference to FIG. 1, a wearable device 104 may interact with a user and/or a remote device using local wireless communications such as but not limited to Bluetooth wireless technology for data transfer and exploiting RSSI levels to determine distances of an individual and or swam, and density of the crowds. Optical cameras sensors can be used to determine distances either from known physical boundaries locations as well as from analyzing the local area that the individual is in. Furthermore, Magnetic Induction, wireless local area network (WLAN), Wi-Fi, near field communications (NFC), wired communications such as wired Universal Serial Bus (USB), and the like. In an embodiment, wearable device 104 may be configured to communicate with remote device using on a Device-to-device (D2D) or thought a Device-to-many architecture using any network and/or any network interface device methodology as described herein. Wearable device 104 may be configured to communicate wirelessly over a network, including any network as described herein. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer, a computing device, and/or a wearable device 104.

With continued reference to FIG. 1, wearable device 104 includes a detection component 112. A "detection component," as used in this disclosure, is a component configured to detect a currently proximate subject 116 in relation to a user 108, wherein the user is in possession of the wearable device 104. A "currently proximate subject," as used in this disclosure, is a human subject, an animal, material or surface, location, setting, surroundings, physical location, and the like, located in an area near a user 108. A currently proximate subject 116 may include a human subject, an animal, material or surface, residue that may be located within a certain distance, mobile device and/or specified location of a user 108. In addition, system may provide feedback as the user is getting closer to the currently proximate subject updating the user from time to time or alerting the user within a specified distance of the currently proximate subject. Feedback can be delivered to the user using sonification, visually with graphics, or text, haptic or photonic. This may include any public and/or private location. For instance, and without limitation, a currently proximate subject 116 may be seated or projected to be seated next to a user 108 on an airplane. In yet another non-limiting example, a currently proximate subject 116 may be standing opposite a user 108 at a private outdoor wedding. The system may be interfaced to Transportation Security Administration (TSA) and other agencies worldwide to validate the user's ability to fly based on susceptibility profile and/or degree of transmission threat as described below in more detail. In yet another non-limiting examples, a user could be inviting a dinner guest over, whereas the user would have knowledge of the user "personal health susceptibility profile and inoculation status" or other status, as well the guest could view the originator susceptibility profile and inoculation status. As defined in this disclosure, an "inoculation status" of a person and/or proximate subject includes a status regarding immunity to a pathogen, including without limitation vaccination status, natural inoculation status as determined by infection history, antibody titers, or the like, and/or status indicating whether the person in question has been invited to opt in to reporting inoculation status, has opted in to reporting inoculation status, has opted out of reporting inoculation status, and/or has partially opted in, such as for instance indication of willingness to report some but not all requested data pertaining to inoculation status, for instance and without limitation as described in further detail below. In yet another non-limiting example, the user could determine where they wish to eat in a geographical area based on asking the system to show the safest (lowest probability of virus/pathogen) location as well as food choices the density of restaurant clients as well as fluctuations in room destiny based on time of day. Reservations may be leveraged to find "best times" for lowest risk exposure. The restaurant may post its sanitization mandate on table distance and mask wearing as well as any reported lack compliance reports. In another example, the system could issue an area-wide and/or hyper-localized "contagion" index, similar to a smog alert. This alert system may be hyper-localized. A "contagion" index may be further refined based on a user's own susceptibility profile and/or a user's own risk of becoming ill and/or developing complications from a pathogen. In yet another non-limiting example, a currently proximate subject 116 may be a known relative and/or friend of a user 108. For example, a currently proximate subject 116 may include a user's grandmother who may visit a user 108 in another state for the user's graduation ceremony. Detection of a currently proximate subject location or projected location 116, may include detecting the presence of the currently proximate subject 116 within a specified location, detecting the distance of the currently proximate subject 116 in relation to a user 108, another currently proximate subject 116, a landmark, and the like. Detection of a currently proximate subject 116 may include detecting data including distance relating to the currently proximate subject 116 as described below in more detail. Currently proximate subject 116 may operate a remote device 120. Remote device 120 may include any processor as described in this disclosure. Remote device 120 may include, be included in, and/or communicate with a mobile device, such as a mobile telephone or smartphone or other IoT device. Remote device 120 may include a single processor operating interpedently, or may include two or more processors operating in concert, in parallel, sequentially, or the like; two or more processors may be included together in a single processor or in two or more processors. Remote device 120 may include a supervisory control and data acquisition (SCADA) information system that may obtain information and/or data from an environmental sensor. Remote device 120 may include but is not limited to, for example, a processor or cluster of processors in a first location and a second processor or cluster of processors in a second location. Remote device 120 may include one or more processors dedicated to data storage, security, distribution of traffic for load balancing, and the like. Remote device 120 may distribute one or more computing tasks as described below across a plurality of processors of processor, which may operate in parallel, in series or in a mesh or star, redundantly, or in any other manner used for distribution of tasks or memory between processors. Remote device 120 may be implemented using a "shared nothing" architecture in which data is cached at the worker, in an embodiment, this may enable scalability of system 100 and/or processor. A user 108 may be in possession of wearable device 104, when wearable device 104 is located on the user 108, in contact with the user 108, in the possession of an article owned by the user 108 such as a briefcase, purse, handbag, and the like or a fixed and or mounted device and/or when wearable device 104 is located adjacent to the user 108, such as when wearable device 104 may be located on a surface next to the user such as a counter, desktop, and the like.

With continued reference to FIG. 1, detection component 112 may include a sensor 124. A "sensor," as used in this disclosure, is a device, module, and/or subsystem configured to detect events and/or changes in an environment, generate, and transmit a signal relating to events and/or changes in an environment. A sensor 124 may be configured to detect a physiological parameter of a user 108 and/or a currently proximate subject 116. A "physiological parameter," as used in this disclosure, is any phenomenon, sign, characteristic, trait, activity, event, and/or feature that may be sensed from a human subject. This may include but is not limited to any biological process, body condition, physiological state, biochemical response, and/or any combination thereof. A physiological parameter may include but is not limited to heart rate or heart beats, heart rate variability (HRV), blood volume pulse (BVP) or blood flow, electrocardiogram signals, volumetric variations of blood volume and/or blood flow, blood oxygen, respiratory rate or breath, brainwave, skin temperature, skin conductivity, eye motion, speech rate, facial expression, body posture, speech, foul language choices, speed of speech communication, volume, cadence, and the like. Sensor 124 may be configured to have one or more methods and/or programming capabilities for calibration and/or validation.

With continued reference to FIG. 1, sensor 124 may include a motion sensor such as an inertial measurement unit, and/or any component that may be included in an inertial measurement unit. As used herein, an inertial measurement unit measures and reports a body's specific force, angular rate, and magnetic field surroundings the body, An inertial measurement unit may include devices such as a gyroscope and/or an accelerometer. A motion sensor may include a gyroscope, which may detect orientation changes of a gyroscope; multiple gyroscopes may detect orientation changes with respect to multiple axes, such as three gyroscopes to detect orientation changes with respect to three axes of rotation, or the like. A motion sensor may include an accelerometer, such as one or more microelectromechanical systems (MEMS) devices. An accelerometer may measure acceleration or position in two or more axes; alternatively or additionally, an accelerometer may include a plurality of accelerometers to detect acceleration with respect to a plurality of axes, such as without limitation three accelerometers that detect motion with regard to three dimensional axes. A motion sensor may include an inertial measurement unit (IMU), which may include multiple types of motion sensors in a single chip or system. A motion sensor may be mounted to one or more parts of user's body to detect motion thereof. Changes in patterns in user motion may indicate a transition by user from one state of wakefulness or sleep to another; for instance, a step towards a deeper sleep state or in a direction transitioning from waking to sleep, as described in further detail below, may be accompanied by a decrease in or cessation of movement by user, and/or by an increased regularity of chest movements indicating regular breathing in a pattern indicative of incipient slumber. A motion sensor may detect changes in patterns of gait, including any locomotion achieved through movement of human limbs. Changes in patterns of gait may include observing differences in limb-movement patterns, overall velocity, forces, kinetic and potential energy cycles, changes in contact with a surface such as the ground or floor and the like.

With continued reference to FIG. 1, a sensor 124 may include a thermal sensor. Thermal sensor may be any sensor that acquires skin temperature of user's body or a portion thereof. Thermal sensor may include a thermometer. Thermometer may be any device that measures temperature. Thermometer may include for example, a mercury thermometer, an electronic thermometer, or an infrared thermometer. Thermal sensor may include, without limitation one or more infrared sensors, which may be composed of thermoelectric/pyroelectric materials or semiconductor devices, such as photodiodes or photoconductors, thermistors, thermocouples, or any other elements or components used in digital and/or electric thermometers or other temperature sensors. Thermal sensor may measure temperature at one or more locations on a user's body. For example, thermal sensor may be placed at or in the mouth, in the ear, in the armpit, and/or in the rectum. Thermal sensor may include non-contact temperature sensors where temperature may be detected or measured remotely, for instance by capturing infrared radiation.

Continuing to refer to FIG. 1, a sensor 124 may include an electrophysiological sensor. An electrophysiological sensor may be any device or component that measures a physiological parameter of a user and generates an electrical signal as a function of the measurement. A physiological parameter may include any information that may be sensed from user's body, including without limitation any electrical, chemical, optical, auditory, olfactory, kinetic, or other information; a physiological parameter may include, without limitation, galvanic skin response or skin conductance response, pulse rate, breathing rate, blood flow, heartbeat signatures, electrolyte type and/or concentration, blood metabolite levels or ratios, blood pH level, position and/or balance, body strain, neurological functioning, brain activity, brain waves, blood pressure, cranial pressure, hydration level, auscultatory information, skin and/or core body temperature, facial emotions, eye muscle movement, body movement, blood volume, inhaled and/or exhaled breath volume, exhaled breath physical and/or chemical composition, reflex response sleepiness, response to external stimuli, swallowing volume, swallowing rate, head position or tilt, internal body sounds, functional near-infrared spectroscopy signals, snoring, and/or other physiological information. Electrophysiological sensor may be utilized to detect a biological parameter such as heart rate, heart rate variability, blood volume, pulse, respiratory rate or breathing rate, brainwaves, skin temperature, skin conductivity, eye motion, speech rate, facial expression, and/or body posture. In an embodiment, sensor 124 may be programmed using one or more algorithms such as but not limited to an acoustic and/or kinetic algorithm to measure certain body functions, including any of the body functions described herein.

Still referring to FIG. 1, an electrophysiological sensor may include, without limitation, a sensor that detects an electrical, magnetic, or electromagnetic parameter, state, or reading regarding body of user. An electrophysiologic sensor may include an electrodynamic sensor device configured to sense an electrical activity of the heart of a user. For example, the electrodynamic sensor may be configured to sense a heart rate or heart rate variability pattern using electrical activity of the heart, for instance using electrocardiography (ECG or EKG), or conductivity. Electrocardiography may include a process of recording electrical activity of a heart over a period of time using electrodes placed on the skin; electrodes may detect tiny electrical changes on the skin that arise from a heart muscle's electrophysiologic pattern of depolarizing during each heartbeat. An ECG may be used to measure rate and rhythm of heartbeats or other patterns relating to heartbeats, including without limitation heart rate variability patterns. Electrodes may be placed in contact with user's skin using any suitable means, including adhesion or incorporation in a wearable device such as a band of elastic material around user's torso, that places electrodes in contact with user's skin. In some embodiments, direct contact may not be necessary, and electrical functioning may be monitored capacitively, inductively, electromagnetically, or a combination of these approaches. Persons skilled in the art, upon reviewing the entirety of this disclosure, will be aware of various ways in which EKG data may be collected consistently with the instant disclosure.

With continued reference to FIG. 1, an electrophysiologic sensor may include a sensor that monitors neurological functioning. As a non-limiting example, electrophysiologic sensor may include one or more sensors that perform an electroencephalogram (EEG); EEG may involve detection of patterns, such as brainwaves, otherwise known as neural oscillations. EEG may be performed by detection of electrical patterns in neural activity using electrodes contacting user's cranium, such as electrodes placed along a forehead of user. Electrodes may be adhered to user or incorporated in a wearable device, such as without limitation an earpiece or item of headgear placing electrodes at cranial locations such as a forehead or temple. In some embodiments, direct contact may not be necessary, and neurological functioning can be monitored capacitively, inductively, electromagnetically, or a combination of these approaches. In some embodiments, brain waves may couple with low frequency acoustical sensors integrated into a head-mounted module, or the like. Persons skilled in the art, upon reviewing the entirety of this disclosure, will be aware of various ways in which EEG data may be collected consistently with the instant disclosure.

Continuing to view FIG. 1, an electrophysiologic sensor may include a sensor configured to perform an electrooculogram (EOG); EOG may be defined as an electrophysiologic measurement of eye motion. EOG may be collected using electrodes mounted at or near user's eyes, for instance through use of a mask or other wearable device that contacts the user's eyelids or rests nearby. EOG may be detected through contactless means such as capacitive, inductive, or electromagnetic detection. Alternatively or additionally, an electrophysiologic sensor may include electrodes or other sensors for monitoring an electromyogram (EMG) signal measuring electrical activity of muscles or muscular tissue of a user. An electrophysiologic sensor may include an electrodermal activity (EDA) sensor, also known as skin conductance, galvanic skin response (GSR) sensor, electrodermal response (EDR) sensor, or the like, which may measure continuous variation in electrical characteristics of skin.

Still viewing FIG. 1, an electrophysiological sensor may include one or more sensors configured to detect arterial or vascular data. For instance and without limitation, an electrophysiological sensor may include a photoplethysmography (PPG) sensor, which may sense the body's rate of blood flow using a light-based technology whereby a light source is emitted through or at tissue containing blood vessels, and light reflected by or transmitted through the tissue is measured. An electrophysiological sensor may include an impedance plethysmograph for measuring changes in volume within an organ or body (usually resulting from fluctuations in the amount of blood or air it contains). For example, an impedance plethysmograph to monitor blood pressure in real-time. An electrophysiological sensor may include a sensor to detect pulse oximetry, where pulse oximetry is a standard noninvasive technique of estimating blood gas levels. Pulse oximeters typically employ two or more optical wavelengths to estimate the ratio of oxygenated to deoxygenated blood. Similarly, various types of hemoglobin, such as methemoglobin and carboxyhemoglobin may be differentiated by measuring and comparing the optical absorption at key red and near-infrared wavelengths. Additional wavelengths may be incorporated and/or replace conventional wavelengths. For example, by adding additional visible and infrared wavelengths, myoglobin, methemoglobin, carboxyhemoglobin, bilirubin, SpCO.sub.2, and blood urea nitrogen (BUN) may be estimated and/or monitored in real-time in addition to the conventional pulse oximetry.

With continued reference to FIG. 1, an electrophysiological sensor may monitor blood pressure, using, as a non-limiting example, a digital blood pressure monitor; digital blood pressure monitor may include actuators and sonic and pressure transducers placed on the skin, and may measure systolic and/or diastolic pressure, for instance by monitoring a pressure at which a "Korotkoff sound" is first heard (systolic), then disappears (diastolic). This technique may also be used to monitor intra-cranial pressure and other internal pressures. Blood pressure may also be measured by comparing the time between pulses at different regions of the body. An electrophysiological sensor may alternatively or additionally include pyroelectric sensor for monitoring heart rate, heart rate variability patterns, and the like.

With continued reference to FIG. 1, a sensor 124 may include an electrodermal sensor such as a galvanic skin response (GSR), electrodermal response (EDR), psychogalvanic reflex (PGR), skin conductance response (SCR), sympathetic skin response (SSR) and/or skin conductance level (SCL). As used herein, an electrodermal sensor measures continuous variations in electrical characteristics of the skin. This may include but is not limited to measurement of sweating response as controlled by a user's sympathetic nervous system. In an embodiment, changes in sweat response and blood flow response may be measured and recorded as changes in electrical conductance between two points over time. Galvanic skin response (GSR) may include placing two electrodes on a user and applying a weak current, resistance and electrodermal activity may then be recorded. In an embodiment, a painful stimulus may elicit a sympathetic response by sweat glands such as an increase in secretion of sweat containing water and electrolytes. This increase in sweat may then lower electrical resistance of the skin and affect GSR readings. Electrodermal dermal sensor may also detect vasodilation of blood vessels, such as for example during exertion when increase sweating occurs and a user's face may turn red.

Continuing to refer to FIG. 1, a sensor 124 may include an acoustic sensor, such as a microphone or the like. An acoustic sensor may detect and/or monitor breathing characteristics of user, for instance via auscultatory signal extraction. In an embodiment, an acoustic sensor may be used to sense sounds associated with breathing, coughing, and variations in coughing such as wet or dry coughs, frequency of coughs, key words, stuttering vomiting, urination, toilet flushing, running water (washing hands), snoring, labored breath, changes in speech cadence and or volume. In an embodiment, an acoustic sensor may measure ambient environmental sounds such as a train crossing a train track or the sound of water running over rocks in a stream. The microphone may also be used with DSP to determine if the user or users in the proximate area are wearing a surgical face mask, a N95 face mask, a KN95 face mask, a respirator, an airline, an oxygen mask, a face shield, or the like. Signal processing algorithms may then be used to extract breathing sounds from other sounds and noise, for instance using digital signal filtering or noise elimination processes. This information may be used, as a non-limiting example, to measure and/or track intensity, volume, and speed of breathing, which may in turn be used to determine a user's state of exertion, and exercise tolerance. Alternatively or additionally, an acoustic sensor may monitor breathing using employ pressure transducers. For instance, and without limitation, changes in pressure inside or near the ear associated with breathing may be measured directly and, through signal processing, translated into a breathing monitor. Similarly, optical reflection sensors may be used to monitor pressure by monitoring physical changes in the skin or tissues in response to breathing. For monitoring the physical changes of the tympanic membrane in response to breathing, and hence ascertaining breathing rate, an optical signal extraction approach may be employed. Microphones can also hear coughing, shortness of breath, troubled breathing indicative of infection such as wheezing, sputtering, shallow respirations, rhonchi, stridor, crackles, bradypneas, apnea, Kussmaul's respirations, Cheyen-Stokes, apneustic breathing, hyperventilation, agonal respirations, and the like.

With continued reference to FIG. 1, a sensor 124 may include a chemical sensor, defined as a sensor that detects airborne chemicals and byproducts, including gases, aerosols, and/or particulate matter. Chemical sensor may be used to detect, without limitation, chemicals consistent with human presence, such as $CO_2$, $H_2$, methane, oxygen, and the like. Chemical sensor may be used to detect one or more volatile organic compounds (VOCs) that may be present in the environment and surrounding locations of a user 108 and/or currently proximate subject 116, including but not limited to carbon dioxide, hydrogen gas, flammable volatiles, and the like. Chemical sensor may be used to detect one or more chemicals that may be disease producing when exposed to a human subject, including but not limited to asbestos, radon, cadmium, benzene, carbon monoxide, soot, lead, mercury, uranium, chlorinated hydrocarbon solvents, carbon disulfide, nitrates, methylene chloride, methyl mercury, cyanide, pesticides, polychlorinated biphenyls (PCBs), carbon tetrachloride, vinyl chloride and the like.

With continued reference to FIG. 1, sensor 124 may include a biosensor, defined as a sensor configured to detect aerosolized bacteria, viruses, and/or fungal spores. A biosensor may detect aerodynamic particle size, particle fluorescence, respirable aerosols, parties, and the like. A biosensor may include an analytical device containing a sensing bioreceptor configured to using optic, electrochemical, and/or piezoelectric technology to detect distinctive analytes such as proteins, and/or nucleic acids indicative of various bacteria, viruses, toxins, fungi, pollen, and the like that may be present in the environment, on a user 108, and/or on a currently proximate subject 116. For instance and without limitation, a biosensor may be configured to detect Human Immunodeficiency Virus (HIV), hepatitis, Ebola, Norovirus, Influenza, Dengue fever, Coronavirus, Epstein Barr virus, Human Papilloma Virus (HPV), Rhinovirus, Japanese encephalitis virus, and the like.

With continued reference to FIG. 1, detection component 112 may include a camera 128. A "camera," as used in this disclosure, is a device that captures pictures, videos, or other visual images. Camera 128 may include for example, an electronic device containing a lens that is used to take pictures. Camera 128 may detect body movement of a user, which may be used similarly to body movements detected by sensor 124; camera 128 may, for instance, capture a sequence of images of user's body and compare images of the sequence of images to determine whether user has moved user's body, and if so, how frequently or to what extent. Camera 128 may detect facial expressions of a user, which may determine whether user is over-exerted or unphased by some sort of physical activity for example. Camera 128 may detect a mask on the user or on the individuals in the area. Camera 128 may be configured to detect density of a location, such as the density of a sports stadium where a user 108 may be located. This may include determining and/or examining the population density of a crowd in an entire location such as the entire sports stadium, and/or the population density of where the user 108 is exactly located within the entire sports stadium. Camera 128 may prompt a user 108 to position camera 128 to point to a certain area or take a photograph of four currently proximate subjects 116 that may be located nearby.

With continued reference to FIG. 1, camera 128 may include an optical camera. An "optical camera," as used in this disclosure, is a device that generates still and/or video images by capturing senses electromagnetic radiation in the visible spectrum, having wavelengths between approximately 380 nm and 740 nm; radiation in this range may be referred to for the purposes of this disclosure as "visible light." Optical camera may include a plurality of optical detectors, where an "optical detector" is defined as an electronic device that device that alters any parameter of an electronic circuit when contacted by visible light. Optical detectors may include, without limitation, charge-coupled devices (CCD), photodiodes, avalanche photodiodes (APDs), silicon photo-multipliers (SiPMs), micro-channel plates (MCPs), micro-channel plate photomultiplier tubes (MCP-PMTs), photoresistors, and/or photosensitive or photon-detecting circuit elements, semiconductors and/or transducers. APDs, as used herein, are diodes (e.g. without limitation p-n, p-i-n, and others) reverse biased such that a single photon generated carrier can trigger a short, temporary "avalanche" of photocurrent on the order of milliamps or more caused by electrons being accelerated through a high field region of the diode and impact ionizing covalent bonds in the bulk material, these in turn triggering greater impact ionization of electron-hole pairs. APDs may provide a built-in stage of gain through avalanche multiplication. When a reverse bias is less than breakdown voltage, a gain of an APD may be approximately linear. For silicon APDs this gain may be on the order of 10-100. Material of APD may contribute to gains.

Still referring to FIG. 1, individual photodetectors in optical camera may be sensitive to specific wavelengths of light, for instance by use of optical filters to exclude such wavelengths; for instance, and without limitation, some photodetectors may be sensitive to blue light, defined as light having a wavelength of approximately 420 nm to 480 nm, some may be sensitive to green light, defined as light having a wavelength of approximately 534 nm to 545 nm, and some may be sensitive to red light, defined as light having a wavelength of approximately 564 nm to 580 nm. Combinations of photodetectors specifically sensitive to red, green, and blue wavelengths may correspond to wavelength sensitivity of human retinal cone cells, which detect light in similar frequency ranges. Photodetectors may be grouped into a three-dimensional array of pixels, each pixel including a red photodetector, a blue photodetector, and a green photodetector. Pixels may be small enough to fit millions into a rectangular array less than an inch across. Optical camera may include one or more reflective and/or refractive components that focus incident light onto photodetectors.

With continued reference to FIG. 1, camera 128 may include an infrared camera. An "infrared camera," as used in this disclosure, is a camera that detects electromagnetic radiation in the infrared spectrum, defined as a spectrum of radiation having wavelengths between approximately 750 nm and 1 mm. As a non-limiting example, infrared camera may detect light in the 0.75 to 1.5 µm range. Infrared camera may include a plurality of infrared detectors, where an "infrared detector" is defined as an electronic device that device that alters any parameter of an electronic circuit when contacted by infrared light. Infrared detectors may include, without limitation, silicon photodiodes doped to detect infrared light and/or microbolometers. A "microbolometer" is defined for the purposes of this disclosure as a specific type of bolometer used as a detector in a thermal camera. Microbolometer may detect infrared light when infrared radiation with wavelengths between 7.5-14 µm strikes detector material, heating it, and thus changing its electrical resistance.

Continuing to refer to FIG. 1, infrared camera may use a separate aperture and/or focal plane from optical camera, and/or may be integrated together with optical camera. There may be a plurality of optical cameras and/or a plurality of infrared cameras, for instance with different angles of perspective on a subject area. Alternatively or additionally, two or more apparatuses coordinated using a mesh network, as described in further detail below, may be combined to generate two or more images from varying perspectives to aid in three-dimensional imaging and/or analysis.

With continued reference to FIG. 1, detection component 112 may be configured to perform simultaneous localization and mapping (SLAM). This may include constructing and/or updating a map of an unknown environment such as a location and tracking a user 108 and/or a currently proximate subject 116 within the location. This may include calculating one or more SLAM algorithms to determine approximations and/or location mapping, including but not limited to particle filter, extended Kalman filter, covariance intersection, and/or GraphSLAM. SLAM may include determining a topology of a room and/or location, mapping an entire location such as every room in a house, obtaining coordinates, evaluating ceiling height and furniture placement within a location, to generate a 3 Dimensional map of a location. Employment of SLAM may include but is not limited to employment of lidar technology. Lidar technology may include measuring distances within a location by measuring distances and/or ranges by illuminating a target with a laser light and measuring the reflection with a detection component 112 such as a sensor 124 and/or a camera 128. This may include imaging, acoustic, radar, lidar, time-of-flight, and/or other sensors 124 and/or cameras 128 configured to detect and map a location, including human subjects and/or animals that may be present in a location. In an embodiment, this may include detecting and/or imaging using radio frequencies including terahertz or millimeter wave imagers, seismic sensors, magnetic sensors, weight/mass sensors, ionizing radiation sensors, and/or acoustical sensors, to accurately recognize and spatially determine a location and/or human subjects and/or animals. This may include, but is not limited to stereo imaging, photogrammetry, time of flight methods, structured light, shape from motion, shape from polarimetry, lidar, radar, sonar, synthetic aperture imaging, multiple disparate apertures, gated imaging, single or multiple pixel range finding, artificial intelligence methods, and/or other methods.

With continued reference to FIG. 1, information captured relating to a currently proximate subject 116 may be collected under certain conditions where the currently proximate subject 116 may be forced to consent to have data captured and/or collected about themselves. For instance, and without limitation, this may occur with an email plug in, such as when a currently proximate subject 116 may be known to be dangerous and/or a public health threat. In yet another non-limiting example, this may occur when a government agency or municipality may require greater transparency relating to personal information, such as for example during natural hazards such as an earthquake, a tsunami, a pandemic, an act of terrorism, and the like. In an embodiment, information may be captured about a user 108 and/or a currently proximate subject 116 based on various situations where the user 108 and/or currently proximate subject 116 may consent because of a benefit and/or reward. In an embodiment, a user 108 may consent to information being shared for a situation such as when at the airport, while the user 108 may not consent to information and/or select information being shared when the user is at a public establishment. For instance and without limitation, the TSA may obtain information such as a degree of transmission threat about a user 108 and/or a currently proximate subject 116 as a way to fast track an approval for the user 108 and/or the currently proximate subject 116 to board a flight. Such information may also be utilized to determine the best location for a user 108 and/or a currently proximate subject 116 to sit on an airplane, on another mode of public transportation such as a bus or train, and/or at a stadium for a sporting event, concert, or any other various forms of entertainment, based in part on the individual's personal health susceptibility profile. In an embodiment, governmental agencies may use information pertaining to possible degrees of threat calculated by wearable device 104 to create rules, laws, enforce rules and/or laws, create context specific procedures, allow flexibility, and create clear and/or predictable results. In an embodiment, governmental agencies and/or concerned parties may be able to track information and/or trends obtained by wearable device 104, but may have limited and/or no access to any personal health information (PHI), and/or identifying information about a user 108 and/or a currently proximate subject 116 that may be stored and/or contained within wearable device 104 and/or an external database. For instance and without limitation, during a pandemic, a governmental agency such as the Department of Homeland Security may access data stored, calculated, and/or contained within wearable device 104 to evaluate trends and/or outbreaks within certain geographical locations, among certain demographic populations, within certain communities and the like. In such an instance, such information accessed by a governmental agency may not contain any identifiable information, and/or information that may breach security laws such as but not limited to the Health Insurance Portability and Accountability Act (HIPAA).

With continued reference to FIG. 1, camera 128 may be configured to detect a user 108 and/or a currently proximate subject 116 wearing personal protective equipment (PPE) such as but not limited to respiratory protection such as a surgical face mask, a N95 face mask, a KN95 face mask, a respirator, an airline, an oxygen mask, a face shield and the like, eye protection such as spectacles, goggles, shields, visors, and the like, hearing protection such as ear muffs, ear plugs, and the like, hand protection such as gloves, mittens, insulated gloves, wire mesh gloves, latex, vinyl, and/or nitrile gloves, chemical resistant gloves, and the like, foot protection such as shoes, boots, shoe covers and the like, head protection such as helmets, caps, hoods, hats, and the like, skin protection such as scrubs, surgical gowns, and the like. This may be useful, such as if a hospital needs to monitor non-professional staff, and/or visitors to deal with challenges presented in nosocomial settings. In an embodiment, PPE such as a mask may be detected based on information such as telephone use, facial recognition, speaker recognition including with or without wearing a mask and the like. Camera 128 may be configured to detect and/or compute a compliance value of a user 108 and/or a currently proximate subject 116 who may be wearing an item of PPE. A "compliance value," as used in this disclosure, is a score indicating how well a user 108 and/or a currently proximate subject 116 may follow recommended guidelines, instructions and/or usage of equipment. For instance and without limitation, a compliance value may specify that a user 108 is wearing a piece of PPE such as a facemask, but the user is not wearing the facemask correctly, and as such the compliance value may indicate a low compliance with a recommendation to wear a facemask. Information pertaining to a compliance value may be stored within user database, as described below in more detail. A compliance value may contain a numerical, character, and/or reference value score associated with a user's 108 and/or currently proximate subject's 116 compliance with a recommendation. For instance and without limitation, a compliance value may be scored on a numerical continuum, where a score of 0 may indicate a user who has very little if any compliance with a recommendation and/or guideline, while a score of 50 may indicate a user who has moderate compliance, and a score of 100 may indicate a user who has very high compliance. In an embodiment, camera 128 may detect a compliance value of a user 108 and/or a currently proximate subject 116 who may be located adjacent to the user 108 for example, as means to detect and ascertain if the currently proximate subject 116 is wearing a mask. In an embodiment, sensor 124 may be utilized to detect and perform a fast Fourier transformation (FFT) analysis on audio that may be captured, such as a phone call to determine if a user 108 and/or a currently proximate subject 116 is wearing a mask and if that can be determined based on audio that may be detected. In an embodiment, a mask may be produced to contain an RFID, NFC, and/or BTLE tag that may inform wearable device 104 if user 108 and/or currently proximate subject 116 is wearing a mask. In an embodiment, PPE equipment may contain a microphone that may detect a sonic signature that may identify use and/or compliance with PPE equipment.

With continued reference to FIG. 1, detection component 112 may be configured to detect a baseline location measurement. A "baseline location measurement," as used in this disclosure, is an initial assessment of a location, to be utilized for future comparisons. A "location," as used in this disclosure, is a place and/or position where a user 108 and/or a currently proximate subject 116 may be located. A location may include a public and/or private permanent or transient site. For example, a location may a specific room at a private residence where a party may be hosted. In yet another non-limiting example, a location may include a transient site, such as a ferry that travels back and forth between an island and mainland. Wearable device 104 may include location component 132. A "location component," as used in this disclosure, is a component that aids in the identification of a location. In one embodiment, the location component exploits received signal strength indicator (RSSI) and other signal strength methodologies to determine the proximity of the proximate individual or swarm. RSSI may include an estimated measure of power level and/or signal that wearable device 104 may receive and/or detect from a device belonging to a currently proximate subject 116, such as remote device 120. At a larger distance, a signal may get weaker and wireless data may get weaker, leading to a lower overall data throughput. A signal may be measured by RSSI which may indicate how well wearable device 104 can hear and/or detect a currently proximate subject 116. In an embodiment, RSSI may be measured with numerical outputs, where the greater the RSSI value, the stronger the signal. For example, an RSSI value represented in a negative numerical value such as −53, the closer the RSSI value is to 0, the stronger the received signal has been. In an embodiment, signal strength may be detected and/or measured based on factors such as physical obstructions, competing Wi-Fi networks, other electronic devices, and the like. This may include the use of detecting Bluetooth signals and/or signal strength, 3G, 4G, and 5G technology, micro cells, and/or macro cells. A location component 132 may include a global positioning system (GPS) which may identify the exact whereabouts of a location, using signals from a satellite. A GPS may identify the address of where a user 108 and/or a currently proximate subject 116 may be located. A GPS may identify the longitudinal and latitudinal coordinates of where a user 108 and/or a currently proximate subject 116 may be located. A GPS may identify a geographical area where a user 108 and/or a currently proximate subject 116 may be located. For instance, and without limitation, a GPS may identify that a user 108 is located in the Pacific Northwest region of the United States. A location component 132 may identify a location using an internet protocol (IP) address, that may identify and extrapolate where a user 108 and/or a currently proximate subject 116 may be located. A location component 132 may identify a location using an internet service provider (ISP) and a corresponding traceroute to identify where a user 108 and/or a currently proximate subject 116 may be located. A location component 132 may identify a location using an International Air Transport Association (IATA) airport code that may be located nearby and/or in proximity to a user 108 and/or currently proximate subject 116. For instance and without limitation, location component 132 may identify a user 108 as being located near IATA code "ORD" which may indicate that the user 108 is located somewhere near Chicago, and thus located in the Midwest region of the United States. In an embodiment, location component 132 may receive an input from user 108 and/or currently proximate subject 116 specifying a location where user 108 and/or currently proximate subject 116 may be located. One or more frequent locations where a user spends a lot of time or repeatedly visits may be saved and stored within user database 136. For instance and without limitation, the address of a user's office building where a user 108 works each day may be stored and saved as "office," while the address of a coffee shop where a user 108 stops and buys coffee from each morning may be saved as "coffee." In an embodiment, information contained within user database 136 may include information describing a user's overall mental and emotional well-being including for example if the user feels anxious or lonely. For example, a user 108 and/or a currently proximate subject 116 may report feeling depressed about a recent national disaster. Information contained within user database 136 may also describe where a user 108 and/or a currently proximate subject 116 may have traveled to, what mode of transportation was utilized, and/or how long a user visited a particular location and where the user visited within the location and what accommodations were employed.

With continued reference to FIG. 1, information relating to a baseline location measurement may be stored within user database 136. User database 136 may be implemented, without limitation, as a relational authorization database, a key-value retrieval authorization database such as a NOSQL authorization database, and/or any other format or structure for use as a user database 136 that a person skilled in the art would recognize as suitable upon review of the entirety of this disclosure. User database 136 may alternatively or additionally be implemented using a distributed data storage protocol and/or data structure, such as a distributed hash table or the like. Data entries in user database 136 may be flagged with or linked to one or more additional elements of information, which may be reflected in data entry cells and/or in linked tables such as tables related by one or more indices in a relational user database 136. Persons skilled in the art, upon reviewing the entirety of this disclosure, will be aware of various ways in which data entries in a user database 136 may be stored, retrieved, organized, and/or be utilized to reflect data and/or records as used herein, as well as categories and/or populations of data consistently within this disclosure.

With continued reference to FIG. 1, detection component 112 is configured to detect a currently proximate subject 116 in relation to a landmark. A "landmark," as used in this disclosure, is a natural and/or artificial feature contained within a location. A natural landmark may include a landmark that is created by and/or relating to nature. For example, a natural landmark may include a tree or stone that may be present in a public location such as a park. In yet another non-limiting example, a natural landmark may include a live plant that may be located atop a table at a restaurant. An artificial landmark may include a landmark that is made and/or produced by mankind and/or machinery. For example, an artificial landmark may include an item of furniture in a lecture hall of a university, such as a desk located in the middle section of the classroom, three rows back from the center stage. A landmark may include a structure such as a school building that may be located in a town. A landmark may include an anatomical structure that may be used as a point of orientation within a location. For example, landmark may include a crack in a ceiling that is uniquely found in a location such as a user's office. A landmark may include an object that may be used as a point of orientation within a location. For example, a landmark may include an object such as a photograph of a replication of the Mona Lisa, which may be located in the waiting room of a dental office. In an embodiment, a landmark may include a temporal component and/or timestamp that may indicate when a landmark was detected, to account for residency placement and/or duration of a landmark. Detection component 112 may detect and store information relating to a currently proximate subject 116 in relation to a landmark, within currently proximate subject database 140. Currently proximate subject database may be implemented as any data structure suitable for use as user database 136, as described above in more detail. In an embodiment, detection component 112 may detect the location of currently proximate subject 116 in relation to landmark and/or user 108. For instance, and without limitation, detection component 112 may detect that a user 108 is located six feet away from landmark, while currently proximate subject 116 is located eight feet away from landmark, and two feet away from user 108. Information relating to location of currently proximate subject 116 in relation to landmark and/or user 108 may be utilized to provide information to a user regarding mitigation components and protected locations, as described below in more detail.

With continued reference to FIG. 1, detection component 112 is configured to detect a first currently proximate subject 116 in relation to a second currently proximate subject 116. Detection component 112 may detect the location of a first currently proximate subject 116 within a location, in relation to a second currently proximate subject 116 within the location. Information relating to location of first currently proximate subject 116 and/or second currently proximate subject 116 may be stored and contained within currently proximate subject database 140. For instance and without limitation, detection component 112 may detect that a first currently proximate subject 116 such as a guest at a wedding reception, is located three feet away from a second currently proximate subject 116 such as the bride, at an outdoor wedding tent located in Bangor, Me. In yet another non-limiting example, detection component 112 may detect that a first currently proximate subject 116 such as a first child located in a classroom in Dallas, Tex., is sitting at a desk located eight feet away from a second currently proximate subject 116 such as a second child located in the same classroom. Detection component 112 may be configured to detect the location of a user 108 in relation to a first currently proximate subject 116, a second currently proximate subject 116, and/or a plurality of currently proximate subjects 116, and quantify risk of currently proximate subjects 116 based on specified distances that may indicate increased risk and/or harm to user 108. Detection component 112 may be configured to triage and detect currently proximate subjects 116 that may indicate the greatest risk of harm and/or contagion for a user. For instance, and without limitation, detection component 112 may detect a location that contains a plurality of currently proximate subjects 116, such as a birthday party that has fifty guests crowded into a living room. In such an instance, detection component 112 may detect that forty of the fifty guests do not pose any real harm to the user 108, because all forty of the guests have left the living room and are now located in the backyard. However, of the ten remaining guests in the living room, three may be of high risk in relation to the user 108, because they are located within three feet of the user, while seven may be of low risk, because they are located twelve feet away from the user 108. In an embodiment, detection component 112 may evaluate the distance between the three-party guests to one another and also evaluate the distance between the three-party guests and the user 108. In yet another non-limiting example, detection component 112 may be configured to detect a baseline location measurement of a baseball stadium, which may contain several thousand fans. In such an instance, detection component 112 may stratify risk, but first detecting a currently proximate subject 116 who may be seated next to a user 108, as compared to another currently proximate subject 116 who may be located 500 yards away, on another side of the baseball stadium.

With continued reference to FIG. 1, wearable device 104 may be utilized to determine trends of pathogens and/or outbreaks of various diseases that may be occurring to a group of one or more users 108 and/or currently proximate subjects 116 and may aid in creating context awareness solutions. For instance, and without limitation, a group may consist of a classroom of kids at a school and the teacher of the classroom. Wearable device 104 may be utilized to determine and assess pathogens and/or diseases that the group may be at risk for. In such an instance, wearable device 104 may evaluate what occurs when a group member leaves the environment of the group, and potentially introduces a pathogen and/or risk of exposing the pathogen. For example, a parent may wish to send a child to school during an outbreak of a pathogen such as influenza, whereby the parent may be concerned that the child may be asymptomatic and may be exposed to influenza and carry the disease back home, thereby infecting the parent and other family members, neighbors, and friends, as well as any other students, teachers, and/or animals that the child may come into contact with. In such an instance, wearable device 104 may be employed by the school so that each student and teacher may be engaged in using wearable device 104 when in school and at home. Information regarding secondary locations visited by children, teachers, workers, cleaning crew, and the like may be stored and utilized by wearable device 104 to provide information regarding an outbreak, and as a means to trace back to the site of the outbreak. In an embodiment, a parent may be notified about an outbreak and the parent may decide if the parent wishes to send their child to school. In an embodiment, a child may only be a carrier of a pathogen and/or disease, and a parent may make a decision about risk and overall transmission rates. In yet another non-limiting example, wearable device 104 may aid in creating contextual awareness solutions regard swarms of individuals in highly dense populations and/or situations that have large numbers of individuals in attendance, including sporting events, concerts, protests, rallies, parades, celebrations, holiday gatherings and the like. For instance and without limitation, wearable device 104 may be used to make informed decisions for a user such as if there may be a possibility of a user contracting a communicable disease such as influenza if the user attends a Fleetwood Mac concert at an indoor concert hall. In yet another non-limiting example, wearable device 104 may be configured to assess how long a group of people have been located in close proximity and may alert a user when certain time criteria have been met. In an embodiment, context awareness solutions may contain timestamps and/or a temporal attribute, describing the duration of a degree of threat. In an embodiment, a degree of transmission threat may be calculated before a user attends the concert, using information available concerning the event, seating arrangements at the event, prevalence of a communicable disease circulating at the event, air flow and ventilation at the event, and the like.

With continued reference to FIG. 1, wearable device 104 may aid in creating a safety profile for intimacy. For example, a wearable device 104 may alert a user 108 about the safety and/or wellness of a currently proximate subject 116 and the risk of acquiring a sexually transmitted infection from a potential partner. For instance and without limitation, wearable device 104 may alert a user 108 who may be located at a bar and around a great number of potential suitors, about the safety and/or risks that may come with engaging in a sexual relationship with a potential suitor. This may allow a user 108 to make an informed decision about if a potential partner is being truthful, what types of sexually transmitted infections the user 108 may be at risk of getting, and/or potential sexually transmitted infections a potential partner may be immune to.

With continued reference to FIG. 1, wearable device 104 may empower a user 108 to make an informed decision regarding all aspects of dating, courtship, and/or relationships. For example, wearable device 104 may be utilized to evaluate a degree of transmission threat if a user 108 were to engage in an act such as holding hands with a currently proximate subject 116 versus the degree of transmission threat if a user 108 were to kiss the currently proximate subject 116. In yet another non-limiting example, wearable device 104 may be utilized to determine the risk of more intimate situations, such as engaging in sexual intercourse with a currently proximate subject 116 as opposed to merely holding hands with the currently proximate subject.

With continued reference to FIG. 1, wearable device 104 includes a data input component 144. A "data input component," as used in this disclosure, a component that captures data relating to a currently proximate subject 116. Data may include information captured using detection component 112, including for example sensor 124 and/or camera 128 as described above in more detail. Data input component may be configured to accommodate various privacy settings, including but not limited to general data protection regulation (GDPR), and/or Singapore data collection. In an embodiment, data obtained from a currently proximate subject 116 may be obtained without the permission, knowledge, and/or consent of the currently proximate subject 116. For example, sensor 124 may be configured to detect and record the temperature of the currently proximate subject 116, without a currently proximate subject 116 being aware of this happening. In an embodiment, information relating to a currently proximate subject 116 may be stored and saved such as in memory, within currently proximate subject database 140. In yet another non-limiting example, information relating to a currently proximate subject 116 may not be stored and may not be saved in memory. In an embodiment, data obtained from a currently proximate subject 116 may be obtained with the permission, knowledge, and/or consent of a currently proximate subject 116. For instance and without limitation, wearable device 104 may transmit to remote device 120, a signal containing an input seeking permission from a currently proximate subject 116 before wearable device 104 measures and/or records the gait and/or movement of the currently proximate subject 116.

With continued reference to FIG. 1, data may include a physiological measurement of currently proximate subject 116. A "physiological measurement," as used in this disclosure is a measurement of a physiological parameter, including any phenomenon, sign, characteristic, trait, activity, event, and/or feature that may be sensed from a human subject. For instance, and without limitation, a physiological measurement may include a measurement of a currently proximate subject's 116 body temperature. In yet another non-limiting example, a physiological measurement may include a recording of a currently proximate subject's 116 breathing patterns to identify any irregularities and/or indicators of illness such as crackles or shallow breathing. In yet another non-limiting example, a physiological measurement may include a photograph of an exposed body part, such as a currently proximate subject's 116 face that may be analyzed for a marker of disease, illness, and/or future likelihood of illness. For instance, and without limitation, a currently proximate subject 116 that appears to have flushed skin particularly on the face and who has rapid perspirations may be at risk of a future likelihood of developing influenza. In yet another non-limiting example, a currently proximate subject 116 that appears to have red, swollen, and itchy eyes may be at risk of developing a coronavirus infection. Data may include information obtained using any sensor 124 as described above in more detail. For example, data may include a measurement using chemical sensor, relating to any by-products that may expelled by currently proximate subject 116, such as for example, any exhaled permanent gases, any volatile organic compounds, any exhaled breath condensate, any proteins, lips, and/or oxidation products, any heavy metals and the like. For example, data may include a measurement of an exhaled breath analysis that may indicate high levels of cysleukotrienes, specifically LTE4, LTC4, and LTD4. Data relating to a currently proximate subject 116 may include a distance measurement between a currently proximate subject 116 and a user 108 in possession of wearable device 104. A distance measurement may specify the amount of space between a user 108 and a currently proximate subject 116. For instance, and without limitation, a distance measurement may specify that a user 108 and a currently proximate subject 116 are located twenty-five feet apart. Distance may be measured using one or more systems of measurement, including but not limited to United States customary units, metric units, imperial units, international system of units, English units, MKS system of units and the like. In an embodiment, a user 108 may preset and select a preferred system of measurement for wearable device 104 to utilize.

With continued reference to FIG. 1, data input component 144 is configured to detect a signal from a device in the possession of a currently proximate subject 116. A "signal," as used in this disclosure, is a function that conveys information. A signal may include a voltage, current, and/or electromagnetic wave, magnetic induction, optical signal, or the like that contains information. In an embodiment, a signal may be received from remote device 120, in possession of currently proximate subject 116, by data input component 144. Data input component 144 identifies an authenticator of a currently proximate subject 116 as a function of the signal. A signal may also contain a distance range a currently proximate subject is from a user. An "authenticator," as used in this disclosure, is participant score of a currently proximate subject 116. A participant score may indicate how much data and/or what types of data may be collected, relating to a currently proximate subject 116. For example, a participant score may indicate that a currently proximate subject 116 agrees to share information with wearable device 104 pertaining to the currently proximate subject's 116 physiological measurements but that the currently proximate subject 116 does not agree to share any personal information with wearable device 104, including any demographic data, personal medical data and the like. In yet another non-limiting example, a participant score may indicate that the currently proximate subject 116 does not agree to share any information with wearable device 104, and as such wearable device 104 may only capture data that may be publicly available. In yet another non-limiting example, a participant score may indicate that the currently proximate subject 116 agrees to share all information with wearable device 104. In yet another non-limiting example, a participant score may indicate that currently proximate subject 116 agrees to share user's susceptibility profile with wearable device 104. Wearable device 104 captures data as a function of an authenticator of a currently proximate subject 116. In an embodiment, a participant score may be used to assess relative risk. For example, someone may want more distance from someone who does not participate in sharing data, because there may be less information known about that person.

With continued reference to FIG. 1, an authenticator may include an indication as to a user's 108 and/or a currently proximate subject's 116 opt-in participation level, with wearable device 104, software run on wearable device 104, data sharing with wearable device 104, data analytics performed with wearable device 104, and the like. In an embodiment, there may be various levels of opt-in participation levels including for example, individuals who have never been exposed to a pathogen of possible contagion 156 before, individuals who have chosen not to opt in, and/or individuals with known statuses, based on calculated degrees of threat as described below in more detail. A known status may include but is not limited to a situation where a user 108 may have been vaccinated, may not be vaccinated, may have confirmed titer indicating immunity to a pathogen based on a vaccination and/or exposure, may not participate, may only participate in select situations, and the like. In an embodiment, a user 108 may initially choose to opt-in, and/or opt-in with certain information such as only inoculation records, whereby later on a user 108 may choose to opt-out and/or not share certain information anymore.

With continued reference to FIG. 1, wearable device 104 includes a processor 148. Processor 148 may include any processor 148 as described in this disclosure, including without limitation a microcontroller, microprocessor, digital signal processor (DSP) and/or system on a chip (SoC) as described in this disclosure. Processor 148 may include, be included in, and/or connect with a mobile device such as a mobile telephone or smartphone. Processor 148 may include a single processor 148 operating independently or may include two or more processor 148 operating in concert, in parallel, sequentially or the like; two or more processors may be included together in a single processor 148 or in two or more processors. Processor 148 may interface or connect with one or more additional devices as described below in further detail via a network interface device. Processor 148 may be located remotely from wearable device 104. Network interface device may be utilized for connecting processor 148 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two processors, and any combinations thereof. A network may employ a wired and/or a wireless mode of communication. In general, any network topology may be used. Information (e.g., data, software etc.) may be transmitted to and/or from a computer and/or a processor 148. Processor 148 may include but is not limited to, for example, a processor 148 or cluster of processors in a first position and a second processor 148 or cluster of processors in a second position. Processor 148 may include one or more processors dedicated to data storage, security, dispersal of traffic for load balancing, and the like. Processor 148 may distribute one or more computing tasks as described below across a plurality of processors of processor 148, which may operate in parallel, in series, redundantly, or in any other manner used for dispersal of tasks or memory between processors. Processor 148 may be implemented using a "shared nothing" architecture in which data is cached at the operative, in an embodiment, this may enable scalability of system 100 and/or processor 148.

Continuing to refer to FIG. 1, processor 148 may be designed and/or configured to perform any method, method step, or sequence of method steps in any embodiment described in this disclosure, in any order and with any degree of repetition. For instance, processor 148 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Processor 148 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 148 is configured to calculate a degree of transmission threat 152 between a user 108 and a currently proximate subject 116. A "degree of transmission threat," as used in this disclosure, is an output identifying the likelihood of a potential negative occurrence and/or event occurring to a user 108 by a currently proximate subject 116 and/or a location where the user 108 may be located. A degree of transmission threat may include but is not limited to a threat of and/or from transmission of a pathogen of possible contagion. A degree of transmission threat may include an indication as to a rate of transmission of a pathogen of possible contagion. A potential negative occurrence may include a likelihood of contracting a pathogen of possible contagion 156. A degree of transmission threat may include and/or reflect a potency of a pathogen of possible contagion, mode of transmission including airborne, waterborne, human to human and the like, as well as localized density, personal susceptibility including age, comorbidities, inoculation status, antibody status, blood type, and the like. A degree of transmission threat may be a dynamic value that may be continually assessed, stored, calculated, and/or collected for trend analysis. A "pathogen of possible contagion," as used in this disclosure, is a causative agent of disease. A causative agent of disease includes any deviation from the normal structural or functional state of a human subject. A causative agent of disease may be caused by an external factor including a pathogen, an internal dysfunction, and the like. A causative agent of disease may be identified by reviewing a known pathogen list, which may contain a list of one or more pathogens of possible contagion to check for. Information pertaining to a pathogen list may be stored within pathogen database, as described below in more detail. In an embodiment, a degree of transmission threat 152 may reflect information for a user 108 such as where is a safe place to travel to currently, what places that a user traveled to recently or historically may impact current behavior, and/or what is the safest and/or best overall location for the user 108 to be located presently.

With continued reference to FIG. 1, a pathogen may include an infectious microorganism and/or agent including but not limited to an alga, a bacterium, a fungus, a prion, a viroid, a virus, pollen, and the like. A pathogen may include an infectious microorganism that may be spread through the air, through human to human transmission, through animal to human transmission, through a water supply, through the environment, through surface contamination, and the like. A virus may include an infectious agent that replicates inside living cells of an organism. A virus may infect all types of life forms and host cells, including but not limited to animals, plants, microorganisms, bacteria, archaea, human beings, and the like. A virus may cause a host cell to produce thousands of copies of the virus. A virus may be transmitted in numerous ways, including but not limiting by plants, animals, coughing, sneezing, fecal oral routes, hand to mouth contact, food, water, and the like. A virus may exist as a plurality of shapes, sizes, and morphologies, including but not limited to helical viruses, icosahedral viruses, prolate viruses, envelope viruses, complex viruses, giant viruses, and the like. A virus may be comprised of a piece of genetic material, such as deoxyribonucleic acid (DNA), or ribonucleic acid (RNA) enclosed in a coat of protein. A virus may invade a host cell such as in a user 108 and use components of the host cell to replicate and multiply. A virus may cause an illness or health condition. For instance and without limitation, a virus may include adeno-associated virus, aichi virus, Australian bat lyssavirus, BK polyomavirus, Banna virus, Barmah forest virus, Bunyamwera virus, Bunyavirus La Crosse, Cercopithecine herpesvirus, Chandipura virus, Chikungunya virus, Coronavirus, Cosavirus A, Cowpox virus, Cozsackievirus, Crimean-Congo hemorrhagic fever virus, Dengue virus, Dhori virus, Dugbe virus, Duvenhage virus, Eastern equine encephalitis virus, Ebola-virus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus, Human herpesvirus, Human immunodeficiency virus, Human papillomavirus, Human parainfluenza, Human parvovirus, Human respiratory syncytial virus, Human rhinovirus, Human SARS coronavirus, Human spumaretrovirus, Human T-lymphotrophic virus, Human torovirus, Influenza A virus, Influenza B virus, Influenza C virus, Isfahan virus, JC polyomavirus, Japanese encephalitis virus, Junin arenavirus, KI polyomavirus, Kunjin virus, Lagos bat virus, Lake Victoria Marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, SARS Coronavirus 2, Semiki forest virus, Seoul virus, Simian foamy virus, Simian virus, Sindbis virus, Southampton virus, St. Louis Encephalitis virus, Tick-borne powasan virus, Torque teno virus, Toscana virus, Uukuniemi virus, Vaccinia virus, Varicellazoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus, and the like.

With continued reference to FIG. 1, bacteria may include a type of biological cell. Bacteria may include single celled organisms. Bacteria may contain a tail, known as a flagellum which may aid in movement. Bacteria may include spherical bacteria such as cocci, rod-shaped bacteria such as bacilli, and/or spiral bacteria such as spirilla. A bacterium may include one or more components, including but not limited to a capsule, cell wall, plasma membrane, cytoplasm, DNA, RNA, ribosomes, flagellum, pill, and the like. Bacteria may include prokaryotic microorganisms that may be present in different shapes including for example spheres, rods, and spirals. Bacteria may include for example *Neisseria Meningitides, Streptococcus pneumoniae, Vibrio cholerae* and *Hemophilus influenzae* type b. Bacteria may exist as single cells as well as in certain characteristic patterns. For example, *Streptococcus* may form chains, and *Staphylococcus* may group together in clusters. Bacteria may attach to surfaces and form dense aggregations known as biofilms. Biofilms may contain multiple species of bacteria, protists, and archaea. Bacteria may include both gram positive bacteria and gram-negative bacteria. Gram positive bacteria include all bacteria that take up crystal violet stain used in a gram test, and which then appear to be purple colored when seen through a microscope. Gram negative bacteria cannot retain the crystal violet stain as their peptidoglycan layer is much thinner as compared to gram positive bacteria, making the cell wall more porous and incapable of retaining the crystal violet stain. Gram positive bacteria may aid in classification and subdivision of bacteria and may include certain species including but not limited to bacilli, cocci, *Staphylococcus* catalase positive, and *streptococcus* catalase negative. Gram negative bacteria may include for example, *Escherichia coli, Salmonella, Shigella, Pseudomonas, Moraxella, Helicobaeisseria gonorrhoease, Neisseria meningitidis, Moraxella catarrhalis, Hemophilus influenzae, Stenotrophomonas, Bdellovibrio, Legionella*, Cyanobacteria, Spirochetes, Green sulfur, and the like. Microorganisms may also be categorized by cellular respiration type as either aerobic or anaerobic. Aerobic microorganisms may include any organism that can survive and grow in an oxygenated environment. Anaerobic microorganisms may be able to make energy without oxygen through either lactic acid or alcoholic fermentation.

With continued reference to FIG. 1, bacteria may include species including but not limited to *Actinomyces israelii, Bacillus anthracis, Bacteroides fragilis, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia penumoniae, Chlamydia trachomatis, Chalmydophila psittaci, Clostridum botulinum, Clostridum difficile, Clostridum perfringens, Clostridium tetani, Corynebacterium diphtheriae, Ehrlichia canis, Ehrlichia chaffeensis, Enterococcus faecalis, Enterococcus faecium, Escherichia coli, Francisella tularensis, Haemophilus influenzae, Helicobacter pylori, Klebsiella pneumoniae, Legionella pneumophila, Leptospira species, Listeria monocytogenes, Mycobacterium leprae, Mycobacterium tuberculosis, Mycoplasma pneumoniae, Neisseria gonorrhoeae, Neisseria meningitidis, Pseudomonas aeruginosa, Nocardia asteroids, Rickettsia, Salmonella, Shigella, Staphyloccocus aureus, Staphylococcus epidermidis, Staphylococcus saprophyticus, Streptococcus agalactiae, Streptococcus pneumoniae, Streptococcus pyogenes, Streptococcus viridans, Treponema pallidum, Vibrio cholerae, Yersinia pestis, Stachybotrys chartarum*, and the like.

With continued reference to FIG. 1, a fungus may include a member of eukaryotic organisms that include but are not limited to yeasts, molds, and mushrooms. A fungus may reproduce by spreading microscopic spores which may be present in the air and soil and may be inhaled or come into contact with surfaces of a human body such as through the skin. Fungus may include opportunistic and/or primary fungus. Fungus may cause fungal infections that may include localized infections that affect only one area of the body, such as but not limited to the skin, nails, vagina, mouth, sinuses, and the like. Fungus may cause systemic fungal infections such as an infection that spreads to one or more locations in the body and may affect the entire body as opposed to one localized area. Fungus may include but are not limited to Candidiasis, Cryptococcosis, Aspergillosis, Coccidioidomycosis, Histoplasmosis, Blastomycosis, *Pneumocystis* pneumonia, *Candida Auris, C. neoformans, C. gattii*, Mucormycosis, Mycetoma, Ringworm, Sporotrichosis, Paracoccidioidomycosis, Talaromycosis, Stachubotrys chartarum, Mycorrhiza, and the like.

With continued reference to FIG. 1, a prion may include an abnormal pathogenic agent that can induce abnormal folding of specific normal cellular proteins found in various locations of the body such as the brain. A prion may transmit their misfolded shape onto normal variants of the same protein, and cause disease. A prion may form an abnormal aggregate of proteins such as amyloids, which may accumulate in infected tissue and cause tissue damage and cell death. A prion may cause disease such as but not limited to Creutzfeldt-Jakob Disease, Variant Creutzfeldt-Jakob Disease, Familial Creutzfeldt-Jakob Disease, Sporadic, Creutzfeldt-Jakob Disease, Gerstmann-Straussler-Scheinker Syndrome, Fatal Familial Insomnia, Kuru, Familial spongiform encephalopathy, Variably protease-sensitive prionopathy, Bovine Spongiform Encephalopathy, Chronic Wasting Disease, Scrapie, Transmissible mink encephalopathy, Feline spongiform encephalopathy, Ungulate spongiform encephalopathy and the like.

With continued reference to FIG. 1, a viroid may include an infectious pathogen that may be composed of a short strand of single-stranded RNA that does not contain a protein coating. A viroid may be transmitted mechanically from one cell to another through cellular debris. Viroid families may include Pospiviroidae, and/or Avsunviroidae. For instance and without limitation, a viroid may include but is not limited to Pop sivviroid, Hostuviroid, Cocaviroid, Apscaviroid, Coleviroid, Avsunviroid, Pelamoviroid and the like.

With continued reference to FIG. 1, a causative agent may include a family of one or more diseases, including but not limited to adenoviridae, coronaviridae, picornaviridae, Herpesviridae, hepadnaviridae, Flaviviridae, retroviridae, Orthomyxoviridae, paramyxoviridae, papovaviridae, polyomavirus, rhabdoviridae, polyomavirus, rhabdoviridae, and/or togaviridae. A causative agent may include one or more diseases and the like.

With continued reference to FIG. 1, processor 148 identifies a pathogen of possible contagion 156, using information contained within pathogen database 160. Pathogen database 160 may include any database suitable for use as user database 136 as described above. Pathogen database 160 may include information relating to various risk factors that may identify and/or make a particular pathogen of possible contagion 156 to be likely to be present in a certain location, and/or to be transmitted to a user 108 by a particular currently proximate subject 116. For instance and without limitation, a first currently proximate subject 116 that has recently traveled to Africa may be at risk for transmitting a pathogen of possible contagion 156 such as Yellow Fever, while a second currently proximate subject 116 that has recently traveled to San Francisco, Calif. may be at risk for transmitting a pathogen of possible contagion 156 such as typhus. Pathogen database 160 may contain information relating to certain pathogens of possible contagion 156 that may be more likely to appear in certain demographics of individuals and/or in certain settings and locations. For example, a bacterial infection such as meningitis may be more likely to be prevalent in populations such as young adults, infants less than one year old, and people traveling to Africa. Similarly, a bacterial infection such as meningitis may also be more likely to be found in crowded living conditions such as dormitories, boarding schools, and sleep away camp. Processor 148 may utilize information pertaining to a baseline measurement to assess landmarks and population density within a room or location to assess risk of crowded living conditions, such as if a baseline measurement indicates that a user 108 and/or currently proximate subject 116 are located within a crowded cabin at a sleep away camp, then a pathogen of possible contagion 156 such as meningitis may be identified. Processor 148 may also use data relating to a currently proximate subject 116 to identify pathogens of possible contagion 156. For instance and without limitation, a currently proximate subject 116 who appears to be less than ten years old, may be used to identify a pathogen of possible contagion 156 such as respiratory syncytial virus (RSV), while a currently proximate subject 116 who appears to be over age sixty may be used to identify a pathogen of possible contagion 156 such as a *Staphylococcus aureus* infection. Information pertaining to a pathogen of possible contagion 156 may be retrievable, accessible, interoperable, reusable and the like.

With continued reference to FIG. 1, processor 148 may utilize information relating to location component 132 to aid in identifying a pathogen of possible contagion 156. For instance and without limitation, an outbreak of a disease may be prevalent in one geographical location and not in another. For example, a pathogen of possible contagion 156 such as the bubonic plague may be prevalent in areas of the United States such as Colorado, New Mexico, Arizona, Nevada, Oregon, Idaho, Utah, and Wyoming, while the bubonic plague may not be prevalent in other areas such as Maine, Vermont, New Hampshire, Massachusetts, and Connecticut. Location component 132 may also be used to identify potential environmental toxins and/or exposures to a pathogen of possible contagion 156. For example, certain locations near contaminated job sites or natural asbestos deposits may indicate a great risk of being exposed to a pathogen of possible contagion 156 such as asbestos. In yet another non-limiting example, an outbreak of a disease such as Legionnaire's disease may be attributed to a particular incident in a specific location, such as the Flint water crisis that occurred in Flint, Michigan and triggered an outbreak of Legionnaire's disease. Pathogen database 160 may be updated in real time, to contain updated and accurate information relating to pathogens of possible contagion 156 that may be probable in certain demographic groups, found in certain geographical locations, and/or attributed to one or more risk factors and/or limitations. Such information may be updated in real time, using any network methodology as described herein. In yet another non-limiting example, processor 148 may detect a pathogen of possible contagion 156 such as conjunctivitis using machine-learning analysis of images of a user's eyes and/or by measuring the degree of hemoglobin absorption in visible light incident to the exterior of the eyeball. In such an instance, more hemoglobin may indicate more bloodshot eyes.

With continued reference to FIG. 1, processor 148 is configured to locate a reproduction rate 164 for a pathogen of possible contagion 156. A "reproduction rate," as used in this disclosure, is a value indicating an expected number of cases generated by one case in a given population, where all individuals are susceptible to infection. In an embodiment, a reproduction rate may indicate a context dependent and/or localized susceptibility to infection based on a certain location, environmental conditions, and/or local population of microorganism present within a location. A population may include a population of human subjects proximate to a user 108 in a room, at an event, at a workplace, in a certain geographical location, and the like. A population may include a population of pathogens of possible contagion 156 that may be found in a certain area and/or contained within a regional growth medium. For instance and without limitation, *Mycobacterium tuberculosis* may be found in soil and/or dung. A reproduction rate 164 may indicate a metric that describes the contagiousness and/or transmissibility of pathogen of possible contagion 156. In an embodiment, a reproduction rate 164 may include a basic reproduction number for a pathogen of possible contagion 156, such as for example an R 0 value. In an embodiment, a reproduction rate 164 may be calculated, taking into account a population state where no other individuals are infected and/or immunized naturally and/or through vaccination. In an embodiment, a reproduction rate 164 may be calculated taking into account a population state where other individuals have been infected and/or immunized naturally through exposure and/ or vaccination. A reproduction rate 164 may be calculated using one or more factors including but not limited to environmental conditions, behavior of infected persons, duration of infectivity of affected populations, infectiousness of a pathogen of possible contagion 156, sociobehavioral factors, environmental factors, and the number of susceptible people that an infected person has come into contact with. Information pertaining to reproduction rate 164 and/or one or more factors utilized to calculate reproduction rate 164 may be stored and contained within reproduction database 168. Reproduction database 168 may be implemented as any data structure suitable for use as user database 136 as described above in more detail. Information contained within reproduction database 168 is described in more detail below. A reproduction rate 164 may be output as a numerical score, a character score, a range of scores and the like. A reproduction rate 164 may provide information relating to how likely a pathogen of possible contagion 156 is likely to spread in a given population. For instance and without limitation, a reproduction rate 164 greater than one may indicate that a pathogen of possible contagion 156 is able to start spreading in a population, while a reproduction rate 164 less than one may indicate that a pathogen of possible contagion 156 is not likely to spread in a given population. In an embodiment, a reproduction rate 164 may indicate a dynamic value that may vary based on a particular location. Information may be updated in real time using any network methodology as described herein.

With continued reference to FIG. 1, reproduction rate 164 may include and/or be based in part on data provided by a federal, state, municipal, or other government agency such as the Centers for Disease Control (CDC) and/or by a corporation, non-governmental organization, or the like. Alternatively or additionally, reproduction rate 164 may be calculated using a reproduction machine-learning model. A "machine-learning model," as used in this disclosure, is a mathematical and/or algorithmic representation of a relationship between inputs and outputs, as generated using any machine-learning process. A "machine-learning process," as used in this disclosure, is a process that automatedly uses training data to generate an algorithm that will be performed by wearable device 104 and/or processor 148 to produce outputs such as reproduction rate 164, using inputs such as any factors that may be used to calculate reproduction rate 164 that may be found within reproduction database 168. This is in contrast to a non-machine-learning software program where the commands to be executed are determined in advance by a user and written in a programming language. Wearable device 104 may include a machine-learning component 172. A "machine-learning component," as used in this disclosure, is a component that calculates, generates, and/or performs one or more machine-learning processes. Processor 148 may retrieve a reproduction machine-learning model as a function of an identified pathogen of possible contagion 156. In an embodiment, one or more reproduction machine-learning models may be stored within reproduction database 168. In an embodiment, processor 148 may generate a query to locate a reproduction machine-learning model relating to an identified pathogen of possible contagion 156. A "query," as used in this disclosure, is a datum used to retrieve a reproduction machine-learning model from a data structure, database, and/or model such as from reproduction database 168. For instance and without limitation, a pathogen of possible contagion 156 such as influenza may be utilized to generate a query such as "influenza" or "viral infections." Reproduction machine-learning model may be trained using training data that may be generated using expert inputs, journal articles and publications, previous iterations of generating pathogen machine-learning model and the like. Reproduction machine-learning model may utilize one or more factors that impact reproduction rate 164 of a pathogen of possible contagion 156 as an input and output a reproduction rate 164. One or more factors that impact reproduction rate 164 may be stored within reproduction database 168 as described above. In an embodiment, one or more pathogens of possible contagion 156 may be related to a reproduction machine-learning model. For instance and without limitation, one or more viruses from a family of viruses may be linked to the same reproduction machine-learning model, whereby viruses which are members of the family of coronaviruses including COVID-19, Middle East Respiratory Syndrome (MERS), and Severe Acute Respiratory Syndrome (SARS) may all be queried to a single reproduction machine-learning model relating to coronaviruses. In yet another non-limiting example, one or more bacterial infections from a family of bacteria may be linked to the same reproduction machine-learning model, whereby for example, species such as *S.argenteus, S. arlettae*, and *S. aureus* may all be queried to a single reproduction machine-learning model relating to staphylococci. In yet another non-limiting example, one or more family of pathogens may query to different reproduction machine-learning models. For instance and without limitation, a pathogen of possible contagion 156 such as *Candida albicans* may be queried to a first reproduction machine-learning model, where cutaneous candidiasis may be queried to a second reproduction machine-learning model even though both *Candida albicans* and cutaneous candidiasis both belong to the same family of fungi. Information pertaining to which species and which pathogens of possible contagion 156 may be used to identify particular reproduction machine-learning models may be selected using expert input, including leading scientists, researchers, medical professionals, journal articles, publications, and the like. Processor 148 outputs a reproduction rate as a function of a reproduction machine-learning model, this may be performed using any of the methodologies as described below in more detail.

With continued reference to FIG. 1, processor 148 is configured to calculate a degree of transmission threat 152 as a function of data input component 144 and reproduction rate 164. A degree of transmission threat includes any of the degree of transmission threats as described above in more detail. Processor 148 may calculate a degree of transmission threat 152, using information relating to a user from user database 136. Processor 148 may retrieve an element of user data, which may be stored within user database 136. An element of user data may include information pertaining to user demographic information such as a user's age, gender, occupation, home address, marital status, family status, home living arrangements and the like. For example, user data may indicate that a user 108 is a thirty-six-year-old female who lives at home with the user's spouse, and the user's sixty-six-year-old mother. Such information may be utilized by processor 148 to account for contemporaneous factors such as socioeconomic factors, behavioral factors, and/or environmental factors that may affect and/or impact a degree of transmission threat 152. For example, a user 108 who has an occupation as a kindergarten teacher, may have a stronger immune system from being around young children all day, which may impact a degree of transmission threat 152, by making the user less susceptible to certain illnesses or diseases. In yet another non-limiting example, a user 108 who has a substance abuse disorder may be at greater risk for developing a disease such as hepatitis, while a user 108 who is unemployed and homeless may be at risk for developing a disease such as acute nonspecific respiratory diseases and tuberculosis. An element of user data may also relate to other behaviors and/or socioeconomic factors that attribute to rates and/or risk of disease, including any medical conditions the user may be diagnosed with, immunizations the user may have received, titer levels indicating antibody levels and immunity, diseases a user may have been exposed to and the like. For instance and without limitation, user data may indicate that a user received an immunization measles, however the user's titer level may indicate that the user does not have certain specified levels of antibodies needed to fight off a measles infection should the user become exposed. In such an instance, a user may require a subsequent dose, round, and/or booster of certain immunizations. A titer may also be utilized to evaluate and determine possible pathogens that a user may have previously been exposed to and developed immunity to later infections. For instance and without limitation, a user 108 who developed mumps as a child may have a titer that shows the user 108 has life-long immunity as a result of developing the illness as a child. User data may also indicate what diseases a user may be a risk of developing at some point in the future, such as a user who is exposed to varicella-zoster virus as a child, may be at risk of developing herpes zoster later in life as a result of developing varicella-zoster virus. User data may include lab data and/or lab results pertaining to a user 108 and/or a currently proximate subject 116.

With continued reference to FIG. 1, wearable device 104 may auto-populate information about a user 108, to be utilized when calculating a degree of transmission threat 152. For instance and without limitation, wearable device 104 may auto-populate a user's vaccination and/or inoculation records from a central vaccine database, such as one that may be maintained by a government agency and stored in an encrypted manner. In an embodiment, wearable device 104 may authenticate a user's 108 identify before accessing a user's vaccine records, such as by using authentication component as described in more detail below. In yet another non-limiting example, wearable device 104 may authenticate and access medical records of a user 108 and/or a currently proximate subject 116 to ascertain previous medical conditions a user 108 may have been diagnosed with, and/or other illness a user 108 may have been exposed to and recorded from, to indicate some degree of immunity that may protect the user 108 from subsequent exposures. In an embodiment, a user 108 and/or a currently proximate subject 116 may enter own immunization and/or medical history data, such as by using graphical user interface as described below in more detail. For example, wearable device 104 may prompt a user 108 for information and may ask a user a series of questions such as what medical conditions a user has been previously and/or currently diagnosed with, or what illness did a user have during childhood. For instance and without limitation, wearable device 104 may list a series of illnesses such as croup, varicella, and *pediculus* capitis, and ask the user to select any illnesses that the user previous had and/or acquired. In an embodiment, information contained within a central vaccine database may be encrypted and access to the central vaccine database may be limited to certain access and/or viewing rights. For example, access rights to information contained within a central vaccine database may be determined by inoculation status, local restrictions such as quarantine rules, testing status, state based rules and laws, municipality based rules and laws, and/or business based rules and laws. Access may also be based on user input and/or what a user feels comfortable allowing other individuals to access.

With continued reference to FIG. 1, processor 148 is configured to calculate a degree of transmission threat 152 of a location where a user 108 is located. A degree of transmission threat 152 of a location, may indicate and/or signal to a user an overall degree of transmission threat if a user 108 is to enter a location and/or remain there, based on the location itself and/or one or more currently proximate subjects 116 that may be located at a particular location. For instance and without limitation, a degree of transmission threat 152 of a location may indicate that a location poses a high risk of threat to a user 108 for transmitting a pathogen of possible contagion 156 to the user 108, because of the number of currently proximate subjects 116 located at the location, and a cumulative effect of the risk of the number of currently proximate subjects 116 present at the location. This information may be helpful such as when the first currently proximate subject 116 that a user comes into contact with at the location has a lower overall degree of transmission threat 152. In an embodiment, processor 148 may utilize information obtained using location component 132, baseline location measurements, landmark information, and the like to calculate the degree of transmission threat 152 for a location.

With continued reference to FIG. 1, degree of transmission threat 152 may be calculated using fuzzy membership sets. A "fuzzy membership set," as used in this disclosure, is a classification scheme that assigns members to a particular class using probabilities of being a member of a specified set, as compared to being classified as either belonging to a class or not belonging to a class. A fuzzy membership set may include but is not limited to fuzzy gaussian membership, fuzzy large membership, fuzzy linear membership, fuzzy MS large membership, fuzzy MS small membership, fuzzy near membership, fuzzy small membership, and the like. For instance and without limitation, a degree of transmission threat 152 calculated using a fuzzy membership set may reflect a range of values for a degree of transmission threat 152 that may indicate a specified threat level, as compared to outputting a single degree of transmission threat 152. For instance and without limitation, a degree of transmission threat 152 calculated using a fuzzy membership set may reflect that a first user 108 having a 10-15% degree of transmission threat 152 of contracting rhinovirus from a currently proximate subject 116, may be classified as being low risk, while a second user 108 having a 14-24% degree of transmission threat 152 of contracting rhinovirus from a currently proximate subject 116 may be classified as being low-medium risk. In an embodiment, wearable device 104 may be configured to use a fuzzy membership set for locating a pathogen of possible contagion 156 as well.

With continued reference to FIG. 1, information contained within user database 116 may be used to authenticate the identity of a user, using authentication component 176. An "authentication component," as used in this disclosure, is configured authenticate the identity of a user 108 at timed intervals, while the user 108 is in possession of the wearable device 104. In an embodiment, the identity of a user 108 may be verified by receiving, capturing, and/or authenticating biometric data, which may be referred to herein interchangeably as "biometrics," by detecting, measuring, or otherwise capturing one or more physiological, behavioral, or biological patterns, qualities, or characteristics identifying a particular person; identification may be unique, or may be effectively unique by, for instance, being highly improbable to be replicated by capturing biometrics of a different persons. Physiological qualities may refer to something that a user is, while behavioral qualities may refer to something that a user can do. Wearable device 104 may include a component connected and/or paired to wearable device 104, via a wired or wireless connection, capable of taking, processing, and analyzing biometric authentication of a user 108. Wearable device 104 may include one or more components of hardware and/or software program code for receiving, obtaining, and authenticating a biometric signature of a user 108. Biometric signature may be generated from biometrics using sensor 124 and/or camera 128. Sensor 124 may scan, read, analyze, and/or otherwise obtain a biometric signature produced from a bodily feature of a user 108. Bodily feature may include a face, a finger, a thumb, an eye, an iris, a retina, a blood composition, a skin or tissue, and the like. Sensor 124 and/or camera 128 may include an optical scanner which may rely on capturing an optical image such as a photograph to capture a bodily feature of a user 108. Sensor 124 and/or camera 128 may include capacitive scanners which may use capacitor circuits to capture a bodily feature of a user 108. A capacitive scanner may include an array of capacitive proximity sensors connected to wearable device 104 and electronic signal processing circuits to detect a bodily feature of a user 108. Ultrasonic scanners may use high frequently sound waves to detect a bodily feature of a user 108. Ultrasonic scanners may include an ultrasonic transmitter and receiver. In an embodiment, an ultrasonic pulse may be transmitted over whenever stress is applied so that some of the pulse is absorbed and some is reflected back to a sensor that may detect stress. Intensity of returning ultrasonic pulse at different points on the scanner may result in capturing a particular bodily feature of a user 108. In an embodiment, a biometric signature of a user 108 may be used to decrypt an encrypted private key, encrypted data record, digital signature, or other cryptographically secured or generated identity token associated with a user 108. In an embodiment, authentication component 176 may authenticate and identify a user 108 and/or a currently proximate subject 116 to aid in ensuring accurate security measures. In an embodiment, authentication component 176 such as a biometric authentication of a user 108 may be utilized to authenticate a user's identify before information may be retrieved from within a database and/or that may be stored pertaining to a user, and/or historical interactions between a user and wearable device 104.

With continued reference to FIG. 1, processor 148 may be configured to calculate degree of transmission threat 152 using a machine-learning process. A machine-learning process includes any of the machine-learning processes as described above in more detail. Calculating a machine-learning process may include selecting a pathogen machine-learning model as a function of a pathogen of contagion 156. A pathogen machine-learning model may be implemented as any machine-learning model suitable for use as reproduction machine-learning model as described above in more detail. Pathogen machine-learning model may be trained using training data that may be generated using expert inputs, journal articles and publications, previous iterations of generating pathogen machine-learning model and the like. Pathogen machine-learning model may utilize reproduction rate 164 for a pathogen of possible contagion 156 and data relating to a currently proximate subject as an input and output a degree of transmission threat 152. One or more pathogen machine-learning models may be stored and contained within pathogen database 160. Pathogen machine-learning model Processor 148 may select a pathogen machine-learning model by generating a query, as described above in more detail. For instance and without limitation, a pathogen of possible contagion 156 such as zoonotic influenza may be queried to a pathogen machine-learning model for influenza, while a pathogen of possible contagion 156 such as smallpox may be queried to a pathogen machine-learning model for variola virus. Processor 148 may upload a selected pathogen machine-learning model to wearable device 104. Uploading may include receiving the most current and/or updated version of pathogen machine-learning model, using internet. This may be performed using any network methodology as described herein. Processor 148 calculates degree of transmission threat 152 using an uploaded pathogen machine-learning model. Machine-learning component 172 may aid in uploading pathogen machine-learning model, and/or calculating degree of transmission threat 152, as described below in more detail.

With continued reference to FIG. 1, wearable device 104 includes a user-signaling component 180. A "user-signaling component," as used in this disclosure, is a component configured to generate an output 184 as a function of a degree of transmission threat 152. An "output," as used in this disclosure, is a response generated based on a degree of transmission threat 152. A response may contain an indication as to a currently proximate subject 116's overall threat to the future health and wellbeing of a user 108. A response may indicate on a scale, how dangerous and/or how harmless a currently proximate subject 116 may be to a user. For example, a response may specify that a currently proximate subject 116 is of a low overall threat to a user's overall health and wellbeing. In yet another non-limiting example, a response may specify that a currently proximate subject 116 is of an immediate and high threat to a user 108. A response may contain one or more recommended actions for a user to take. For example, a response when a currently proximate subject 116 is of a very high threat and dangerous may suggest that a user immediately leave the room and to not approach the currently proximate subject 116. A response may contain a recommended mitigation component. A "mitigation component," as used in this disclosure, is a recommendation that may aid in reducing the severity and/or seriousness of a degree of transmission threat 152. A mitigation component 188 may contain a recommendation for an immediate action that a user can take to reduce a degree of transmission threat 152, such as by leaving the location and putting a maximum amount of distance between a user 108 and a currently proximate subject 116. A mitigation component 188 may contain a recommendation for an action that a user can take in the very near future that may help reduce a degree of transmission threat 152 of a currently proximate subject 116. For instance and without limitation, a user may be instructed to immediately leave and go home and consume a one time high dose of Vitamin D after being exposed to a currently proximate subject 116 who poses a very high degree of transmission threat of passing on a pathogen of possible contagion such as rhinovirus. A mitigation component 188 may contain a recommendation for a long-term course of action that a user can take to aid in reducing a degree of transmission threat 152. For example, a user may be instructed to take a course of oseltamivir after being exposed to a currently proximate subject 116 who poses a very high degree of transmission threat of passing on a pathogen of possible contagion such as influenza. Wearable device 104 may be configured to identify a precipitating component relating to a pathogen of possible contagion 156. A "precipitating component," as used in this disclosure, is one or more identifiable conditions that put a user 108 at increased risk of acquiring a pathogen of possible contagion 156, and/or a currently proximate subject 116 at increased risk of transmitting the pathogen of possible contagion 156. An identifiable condition may include certain environmental, behavioral, social, and/or external factors that may relate to a precipitating component. For instance and without limitation, a currently proximate subject 116 who recently traveled to South America, and who did not take prophylactic medication while traveling and/or any necessary precautions, may have an identifiable condition that may put the currently proximate subject 116 at increased risk of transmitting locally endemic diseases such as tuberculosis. In yet another non-limiting example, a user 108 who lives at home with the user's 108 elderly parents may be at increased risk of transmitting a pathogen of possible contagion 156 to the user's 108 parents, including common bacterial infections such as Methicillin resistant *Staphylococcus aureus* (MRSA) and viral infections such as herpes zoster virus. In yet another non-limiting example, a user 108 who takes chronic immunosuppressant medications after having a heart transplant may have a precipitating component of having an increased risk of catching viral and bacterial infections as compared to the human population who are not taking chronic immunosuppressant medications. Wearable device 104 determines a mitigation component 188 configured to reduce a reproduction rate 164 and displays the mitigation component 188. For instance and without limitation, a precipitating component such as a cold and dry winter that commonly occurs in the Northeast section of the United States, make enable viruses such as influenza to more easily reproduce, replicate, and spread during the winter months. In such an instance, wearable device 104 may determine a mitigation component 188 such as recommending the use of a humidifier and high doses of Vitamin D, to aid in reducing the reproduction rate of influenza during the winter months. Wearable device 104 may display the mitigation component 188, such as for example, on graphical user interface 192.

With continued reference to FIG. 1, an output 184 may include a visual output. A "visual output," as used in this disclosure is an output that contains words, symbols, numbers, and/or characters as an output. A visual output may be displayed on a graphical user interface 192. Graphical user interface 192 may include without limitation, a form or other graphical element having display fields, where one or more elements of information may be displayed. Graphical user interface may include sliders that may be displayed and adjusted based on a given degree of transmission threat 152. For instance and without limitation, a user with a high degree of transmission threat 152 may have sliders that contain a visual display illustrating the high degree of transmission threat 152, while sliders may be scaled back and illustrate a lower degree of transmission threat 152 for a low degree of transmission threat 152. Graphical user interface 192 may include free form textual entries, where a user 108 may type in follow up questions or seek to clarify information relating to mitigation components. Graphical user interface 192 may display a series of pictures and/or visuals displaying an output 184 and/or a degree of transmission threat 152. Graphical user interface 192 may display an output 184 and/or a degree of transmission threat 152 as a numerical output that may be based on a scale and/or continuum. For example, an output 184 may quantify a degree of transmission threat 152 on a numerical scale, such as for example a scale from 0 to 100, where an output containing a score of 0 may indicate a very low and/or nonexistent degree of transmission threat while an output containing a score of 100 may indicate a very high degree of transmission threat. In yet another non-limiting example, a degree of transmission threat 152 may be displayed as a percentage such as this currently proximate subject 116 has a 20% risk of transmitting a pathogen of possible contagion 156 to a user 108. In yet another non-limiting example, a degree of transmission threat 152 may be displayed as a graphical representation, including but not limited to a line graph, a pie chart, a bar chart, a histogram, a line chart, a scatter plot, a funnel chart, a waterfall chart, a pictogram, a graph of a function, a pictograph, an organizational chart, a flowchart, a cosmograph, a dual axis chart, an area chart, a stacked bar graph, a mekko chart, a scatter plot chart, a bubble chart, a bullet chart, a heat map and the like. In yet another non-limiting example, graphical user interface 192 may contain one or more mitigation components that may be useful in conjunction with an output 184. Graphical user interface 192 may display an output 184 that may contain character and/or symbolic outputs. For instance and without limitation, an output 184 that communicates a low degree of transmission threat may be displayed as a happy smiling face emoji, to indicate that a currently proximate subject 116 poses very little harm, if any at all to a user 108. In yet another non-limiting example, an output 184 that communicates a high degree of transmission threat may be displayed as a sad face emoji, to indicate that a currently proximate subject 116 poses a very high threat to a user 108. Graphical user interface 192 may display one or more words and/or warning signs to a user 108. For instance and without limitation, graphical user interface 192 may display a message such as "warning do not approach" when a currently proximate subject 116 poses a high degree of transmission threat 152, whereas graphical user interface 192 may display a message such as "safe" when a currently proximate subject 116 poses very little if any degree of transmission threat 152 to a user 108. In an embodiment, a currently proximate subject 116 who poses a moderate degree of transmission threat 152 may cause graphical user interface 192 to display a moderate risk warning containing one or more mitigation components 188 that may aid in reducing a degree of transmission threat 152.

With continued reference to FIG. 1, an output 184 may include a tactile output. A "tactile output," as used in this disclosure, is an output containing a sensory response. A sensory response may include a response directed affecting a sense including but not limited to sight, hearing, smell, taste, and/or touch. A tactile output may include for example an audio alarm that may trigger a certain number of beeps to indicate if a user 108 is near a currently proximate subject 116 who may pose a threat, whereas the audio alarm may not trigger at all if a user 108 is near a currently proximate subject 116 who may not pose a threat. In yet another non-limiting example, a tactile output may include a vibration, whereby wearable device 104 may vibrate in a certain manner or a certain number of times to indicate that the user is near a currently proximate subject 116 who may pose harm or risk to a user 108, whereby wearable device 104 may not vibrate when a currently proximate subject 116 poses no or minimal risk, or may vibrate in a unique manner based on a particular degree of transmission threat 152 that a currently proximate subject 116 may pose. In an embodiment, a vibration may include a buzzing, whereby a particular sequence of buzzing may indicate risk of a potential deadly pathogen of possible contagion. For example, a series of three rounds of buzzing may indicate a high risk of coming into contact with a pathogen of possible contagion such as COVID-19, whereas a series of one round of buzzing may indicate a low and/or nonexistent risk of coming into contact with COVID-19. In an embodiment, wearable device 104 may be programmed to set off a certain series of buzzing and/or vibrations for certain pathogens of possible contagion 156 that may be highly prevalent in a particular area, and/or of great concern to a user 108. In an embodiment, an output may include specific alarms and/or signals to a user 108, such as when the user 108 may come within a certain distance of a currently proximate subject 116, such as within 3 feet, 6 feet, 12 feet and the like. In an embodiment, an output may be programmed to alert a user 108 when the user 108 comes within a certain distance of the currently proximate subject, as predetermined based on a pathogen of possible contagion 156 and/or a user's preference.

With continued reference to FIG. 1, an output 184 may identify a protected location in relation to a user 108. A "protected location," as used in this disclosure, is an area that is considered safe, and where a currently proximate subject poses a reduced and/or very minimal, if any at all degree of transmission threat. A protected location may be located within a location. A protected location may indicate a relatively lower degree of transmission threat, such as a minimal degree of transmission threat for a location and may indicate the best option available for a user 108, if the user 108 is not able to immediately vacate the location. A protected location may be extended to a best path, a path to a best location, a best path to best location and the like. For instance and without limitation, if a user 108 and a currently proximate subject 116 are both located at an outdoor Olympic size swimming pool, a protected location may be identified where the user 108 is located at the first end of the Olympic size swimming pool, and the currently proximate subject is located at the second end of the Olympic size swimming pool. Signaling component 180 and/or wearable device 104 may identify protected locations using information contained from baseline location measurements and/or landmarks. For instance and without limitation, signaling component 180 may identify from a baseline location measurement that a location where a user 108 and a currently proximate subject 116 are located contains several landmarks that can be used to divide the location up into six zones where each zone will measure approximately six feet and maintain enough distance to ensure six people can be comfortably and safely located within the location. In an embodiment, an output 184 may identify a path and/or route of where a user 108 should walk, travel, and/or move within a location to get to a protected location if the user 108 is not at a protected location. For example, graphical user interface 192 may display a suggested route that a user should take at a wedding venue to get to a protected location where the user 108 has put enough distance between the user 108 and a currently proximate subject 116 who poses a moderate degree of transmission threat 152 to the user 108.

With continued reference to FIG. 1, calculation of a degree of transmission threat 152 may not be limited to being performed on a wearable device. In an embodiment, a degree of transmission threat 152 may be displayed on a sign at a public location that may be dynamic, and transient and displayed to patrons who may enter the public location. For instance and without limitation, a degree of transmission threat 152 may be calculated for a restaurant, whereby the degree of transmission threat 152 may be calculated based on the currently proximate subjects 116 located within the restaurant and whereby the degree of transmission threat 152 for the restaurant may be displayed to patrons and potential patrons who seek to dine at the restaurant but may be unsure of the safety of the restaurant and may require reassurances. In yet another non-limiting example, a degree of transmission threat 152 may be calculated and displayed to convey information to one or more members of the public who may be entering and/or leaving a public location, including but not limited to a hotel, a shopping mall, a playground, a park, a zoo, a theater, a store entrance, a fair, and the like.

Figure 2:
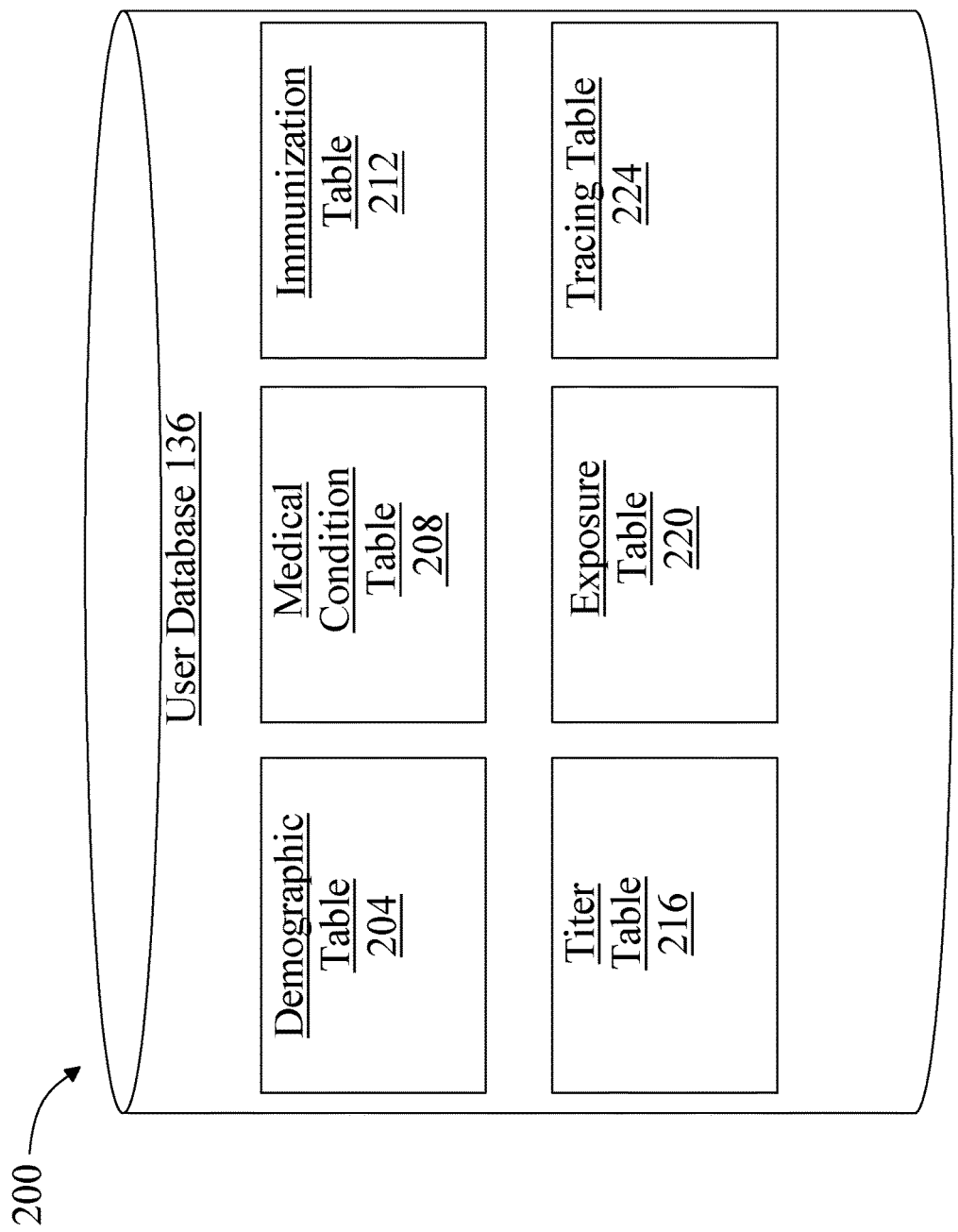
FIG. 2 is a block diagram illustrating an exemplary embodiment of a user database.

Referring now to FIG. 2, an exemplary embodiment 200 of user database 136 is illustrated. User database 136 may be implemented as any data structure as described above in more detail in reference to FIG. 1. One or more tables contained within user database 136 may include demographic table 204; demographic table 204 may contain information relating to demographic information about a user. For instance and without limitation, demographic table 204 may contain information relating to a user's full legal name, date of birth, gender, marital status, income, composition of family household, religion, ethnicity, and the like. One or more tables contained within user database 136 may include medical condition table 208; medical condition table 208 may contain information relating to current medical conditions that a user may be currently diagnosed with. For instance and without limitation, medical condition table 208 may specify that a user suffers from hypothyroidism and ulcerative colitis. One or more tables contained within user database 136 may include immunization table 212; immunization table 212 may include information relating to any immunizations that a user may have received, and on what dates specifically. For instance and without limitation, immunization table 212 may indicate that a user was most recently administered a tetanus booster three years previously. One or more tables contained within user database 136 may include titer table 216; titer table 216 may include information relating to the titer status of one or more antibodies. For instance and without limitation, titer table 216 may indicate that a user has a positive titer status to Hepatitis B, but that the user has a negative titer status to mumps. One or more tables contained within user database 136 may include exposure table 220; exposure table 220 may include information relating to which diseases such as viruses, fungi, viroids, prions, bacteria, and/or viroids that a user may have been exposed to. For instance and without limitation, exposure table 220 may indicate that a user has previously been exposed to influenza A and coronavirus. One or more tables contained within user database 136 may include tracing table 224; tracing table 224 may include information relating to other individuals and/or currently proximate subjects that a user may have come into contact with. For instance and without limitation, tracing table 224 may contain information describing all encounters a user has had with other individuals and/or currently proximate subjects over a specified time period.

Figure 3:
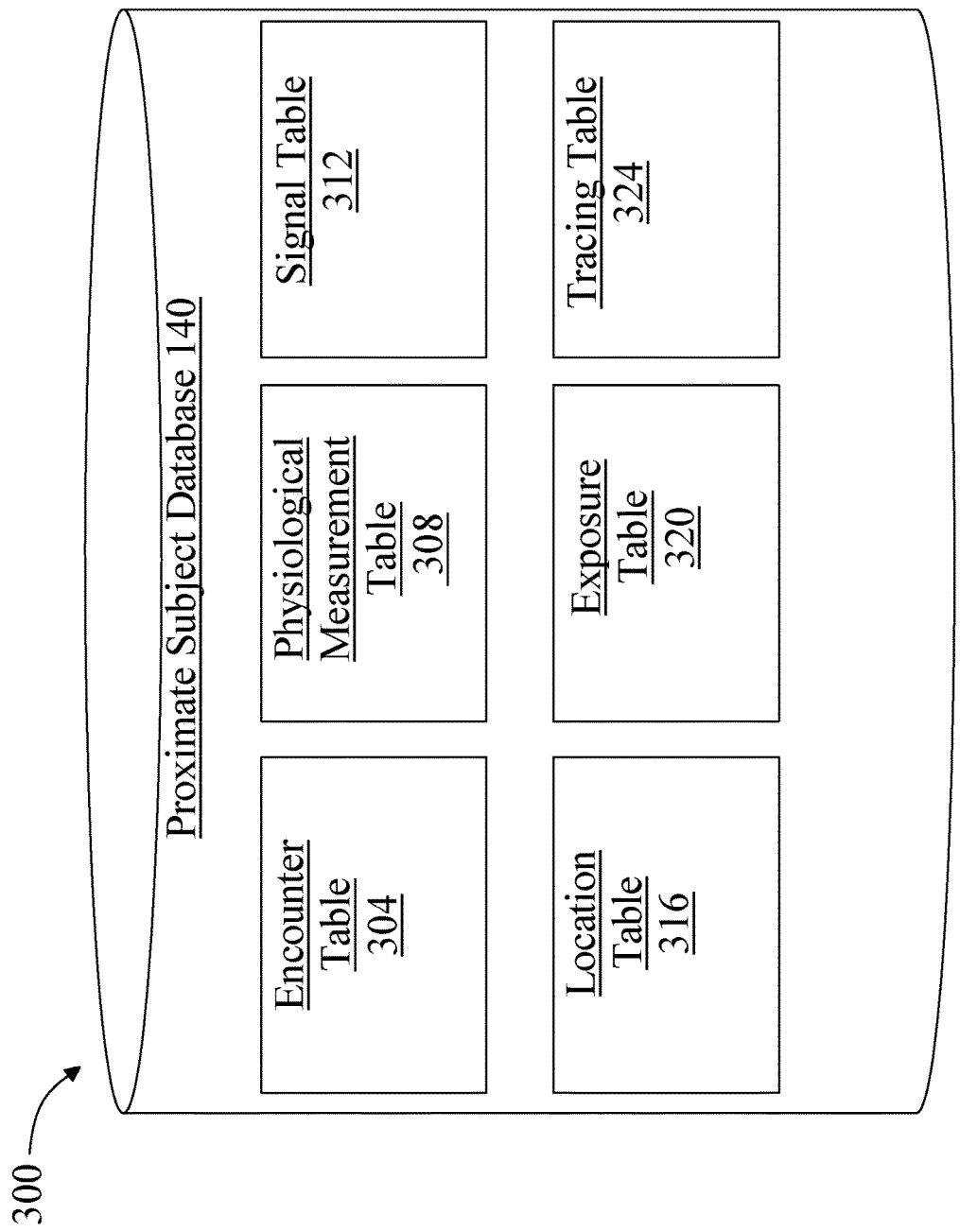
FIG. 3 is a block diagram illustrating an exemplary embodiment of a proximate subject database.

Referring now to FIG. 3, an exemplary embodiment 300 of currently proximate subject database 140 is illustrated. Currently proximate subject database 140 may be implemented as any data structure as described above in more detail in reference to FIG. 1. One or more tables contained within currently proximate subject database 140 may include encounter table 304; encounter table 304 may include information relating to encounters that a currently proximate subject may with have with a user. For instance and without limitation, encounter table 304 may contain information detailing the length of an encounter between a user and a currently proximate subject at a bakery when ordering coffee. One or more tables contained within currently proximate subject database 140 may include physiological measurement table 308; physiological measurement table 308 may include one or more physiological measurements captured from a currently proximate subject. For instance and without limitation, physiological measurement table 308 may contain a measurement specifying that a currently proximate subject has a temperature of 97.9 degrees Fahrenheit. One or more tables contained within currently proximate subject database 140 may include signal table 312; signal table 312 may include information relating to a currently proximate subject's signal. For instance and without limitation, signal table 312 may specify what information a currently proximate subject is willing to share with a user and/or wearable device 104. One or more tables contained within currently proximate subject database 140 may include location table 316; location table 316 may include information describing the location where a user and a currently proximate subject interact. For instance and without limitation, location table 316 may specify that a user and a currently proximate subject interacted at an outdoor wedding in Honolulu, Hi. One or more tables contained within currently proximate subject database 140 may include exposure table 320; exposure table 320 may include information relating to any immunizations, exposures, and/or titer levels of a currently proximate subject that may be known, such as from a government immunization database, publicly available information and the like. For instance and without limitation, exposure table 320 may include information indicating that a currently proximate subject was exposed to H1N1 Swine flu, and the currently proximate subject has a positive titer level to the H1N1 Swine flu. One or more tables contained within currently proximate subject database may include tracing table 324; tracing table 324 may include information relating to other encounters a currently proximate subject may have had with other currently proximate subjects and/or other users. For instance and without limitation, tracing table 324 may include information describing other currently proximate subjects and/or users that a currently proximate subject came into contact with yesterday.

Figure 4:
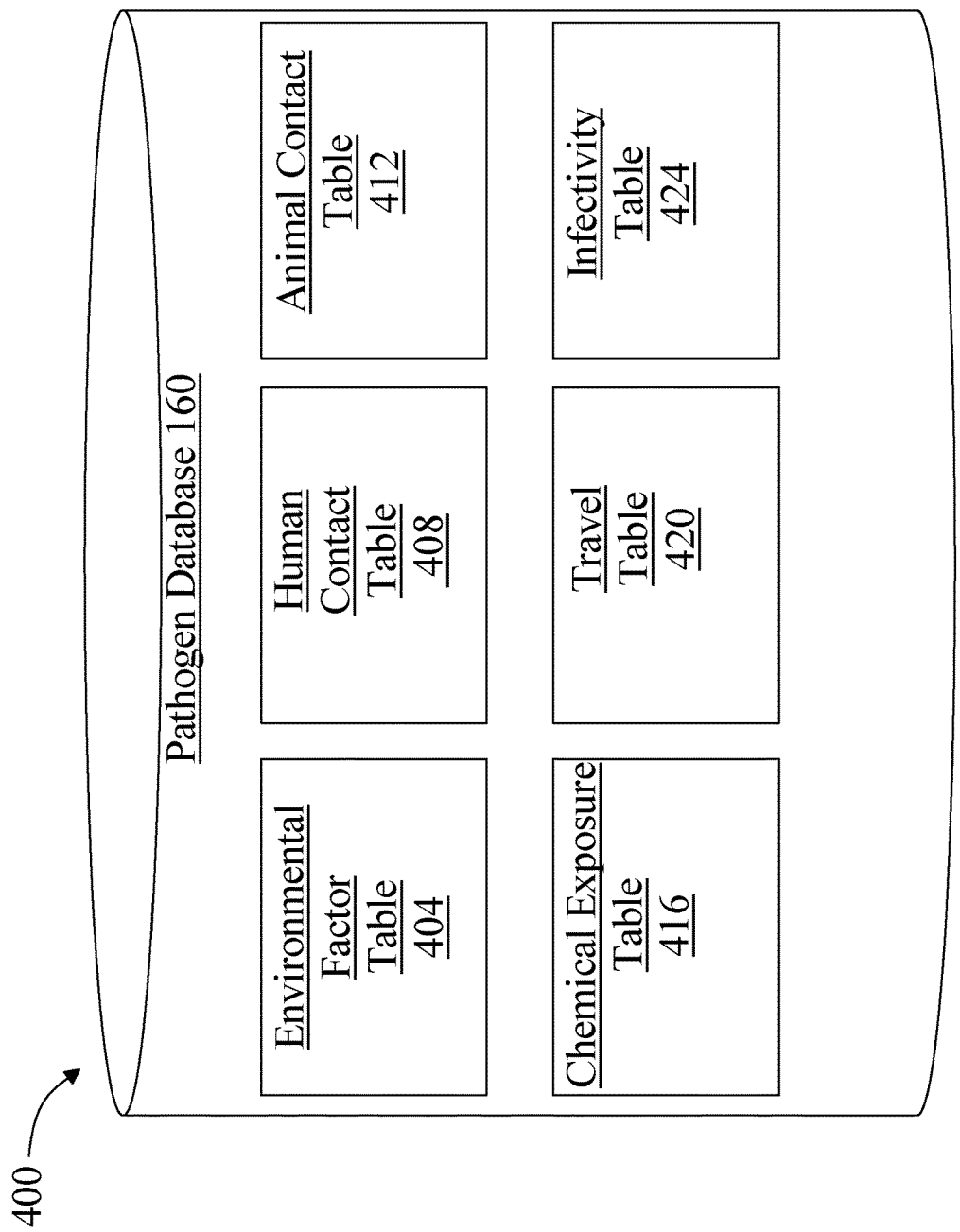
FIG. 4 is a block diagram illustrating an exemplary embodiment of a pathogen database.

Referring now to FIG. 4, an exemplary embodiment 400 of pathogen database 160 is illustrated. One or more tables contained within pathogen database 160 may include environmental factor table 404; environmental factor table 404 may contain information relating to environmental factors that may contribute to prevalence of pathogens of possible contagion. For instance and without limitation, environmental factor table 404 may include information describing flooding and swampy waters that have attributed to breakouts of West Nile Virus in certain areas of the United States. One or more tables contained within pathogen database 160 may include human contact table 408; human contact table 408 may include a list of diseases that are transmitted from human to human contact. For instance and without limitation, human contact able 408 may specify that influenza A may be transmitted from human to human contact and droplet transmission from coughing, sneezing, and talking. One or more tables contained within pathogen database 160 may include animal contact table 412; human contact table 412 may include a list of diseases that are transmitted from human to animal contact. For instance and without limitation, animal contact table 412 may include information listing hantavirus as a virus that can be transmitted from human to animal contact. One or more tables contained within pathogen database may include chemical exposure table 416; chemical exposure table 416 may include information detailing chemical exposures and link of such exposure to disease. For instance and without limitation, chemical exposure table 416 may specify that exposure to certain chemicals in the water and/or air conditioning may lead to development of Legionnaire's disease. One or more tables contained within pathogen database 160 may include travel table 420; travel table 420 may include one or more pathogens that may be prevalent in a particular area where a user and/or a currently proximate subject may have recently traveled to. For instance and without limitation, travel table 420 may specify that diseases such as Lyme Disease and Eastern Equine Encephalitis may be prevalent in the North Eastern region of the United States, particularly in the warmer summer months. One or more tables contained within pathogen database 160 may include infectivity table 424; infectivity table 424 may include the information relating to the infectivity of a pathogen of possible contagion. For instance and without limitation, infectivity table 424 may specify that a pathogen of possible contagion such as Ebola virus is transmitted through contact with bodily fluids such as blood.

Figure 5:
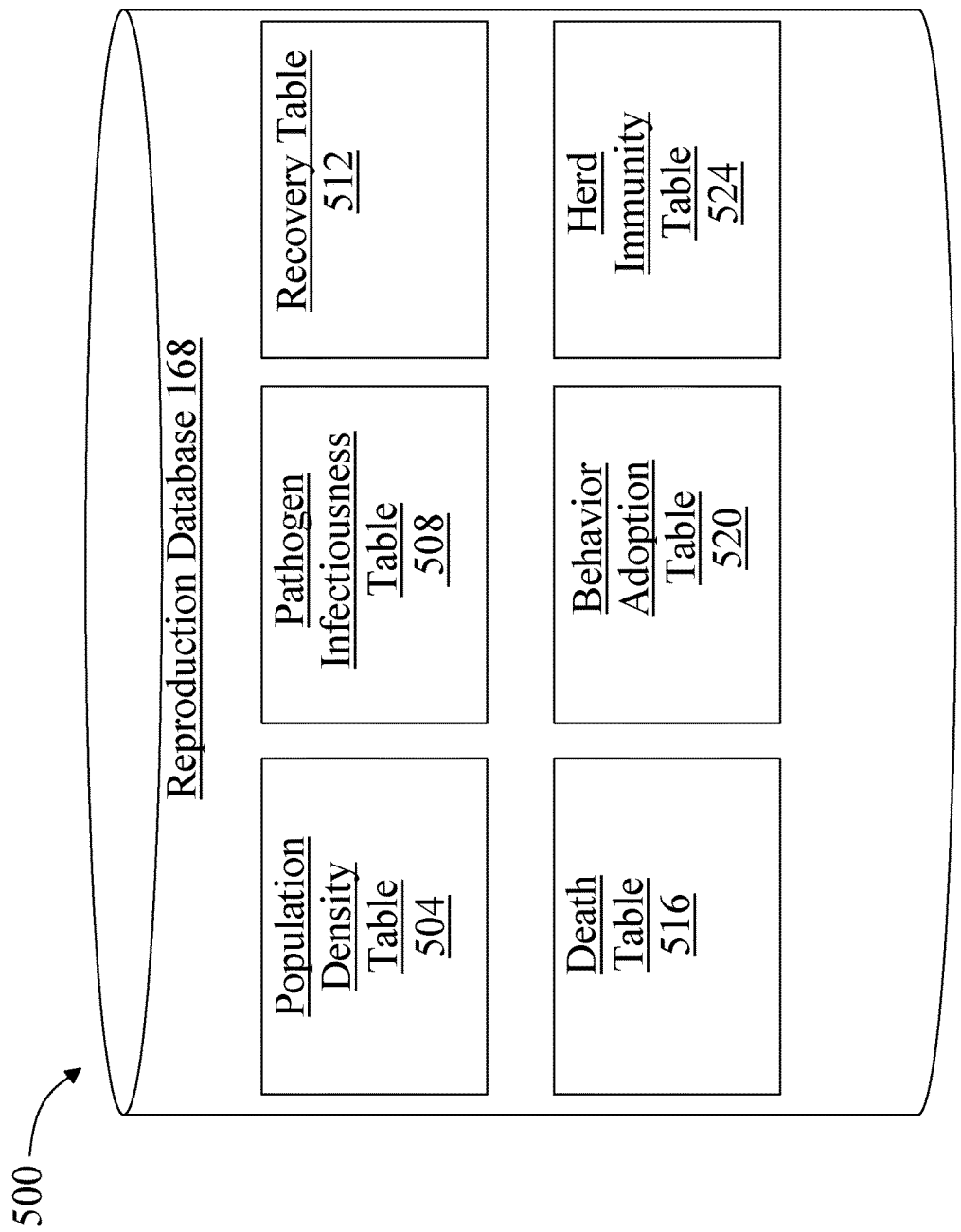
FIG. 5 is a block diagram illustrating an exemplary embodiment of a reproduction database.

Referring now to FIG. 5, an exemplary embodiment 500 of reproduction database 168 is illustrated. Reproduction database 168 may be implemented as any data structure suitable for use as described above in more detail in reference to FIG. 1. One or more tables contained within reproduction database 168 may include population density table 504; population density table 504 may include information detailing the population density of one or more locations. For instance and without limitation, population density table 504 may include information detailing the population density of a location such as the city of Orlando, Fla. One or more tables contained within reproduction database 168 may include pathogen infectiousness table 508; pathogen infectiousness table 508 may include information relating to how infectious a particular pathogen of possible contagion may be. For instance and without limitation, pathogen infectiousness table 508 may specify that a pathogen of possible contagion such as measles is highly contagious, whereas a pathogen of possible contagion such as shingles is less contagious. One or more tables contained within reproduction database may include recovery table 512; recovery table 512 may include information relating to the number of people who have recovered from a pathogen of possible contagion. For instance and without limitation, recovery table 512 may specify that during the 2019 flu season, 9 million Americans recovered from influenza A and influenza B. One or more tables contained within reproduction database may include death table 516; death table 516 may indicate how many human beings have died as a result of a pathogen of possible contagion over a specified time period. For instance and without limitation, death table 516 may specify that 9,000 human beings have died during 2020 in Massachusetts from COVID-19 infections. One or more tables contained within reproduction database 168 may include behavior adoption table 520; behavior adoption table 520 may include information relating to behaviors that may impact the reproduction rate for a pathogen of possible contagion. For instance and without limitation, behavior adoption table 520 may specify that hygienic practices such as handwashing can reduce reproduction rates of rhinovirus by 50%. One or more tables contained within reproduction database 168 may include herd immunity table 524; herd immunity table 524 may include information relating to levels of herd immunity that have been achieved in certain locations for specified pathogens of possible contagion. For instance and without limitation, herd immunity table 524 may indicate that 20% of the population in the state of Rhode Island has achieved immunity to a pathogen of possible contagion such as parainfluenza.

Figure 6:
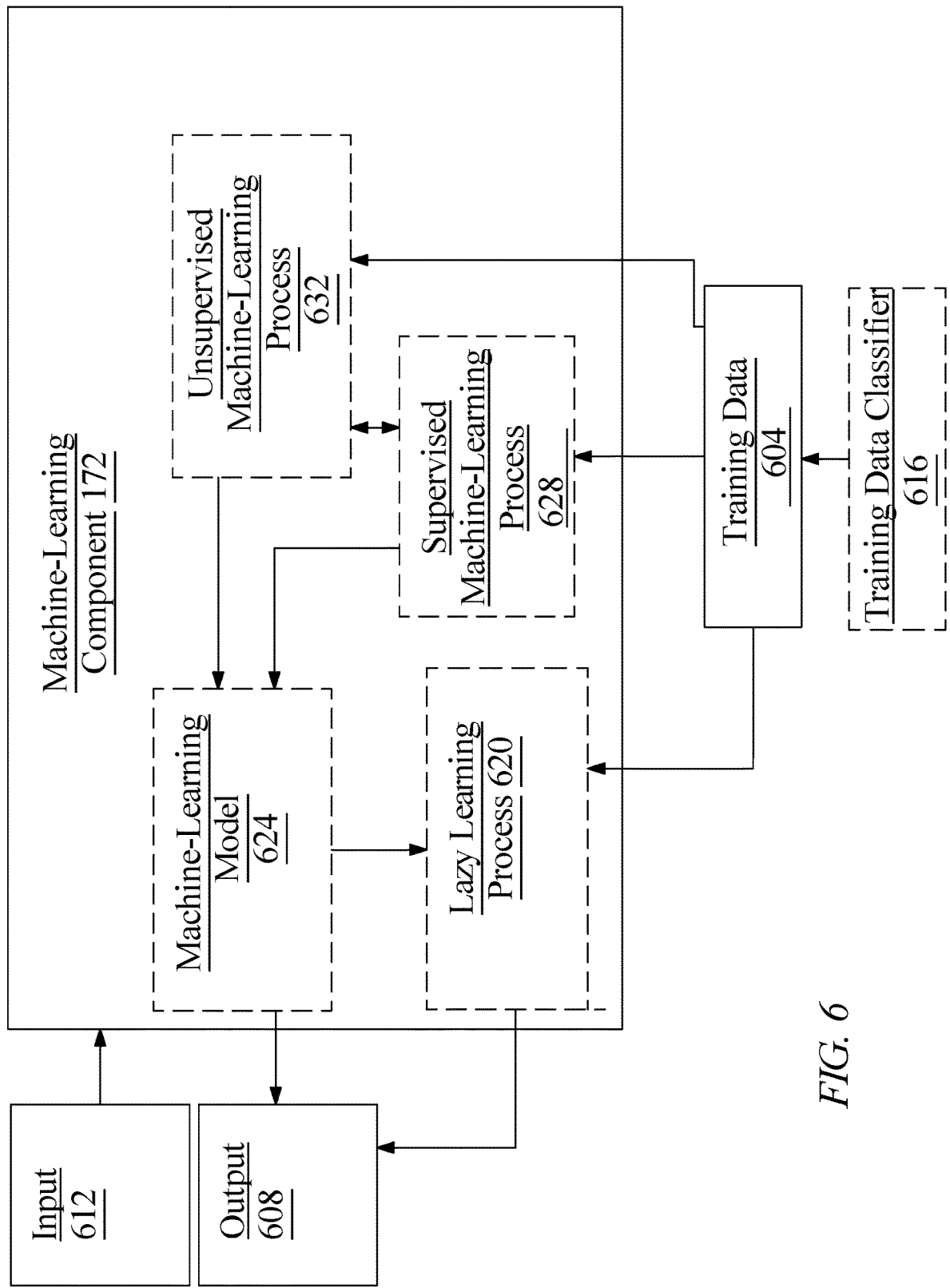
FIG. 6 is a block diagram illustrating an exemplary embodiment of a machine-learning component.

Referring now to FIG. 6, an exemplary embodiment 600 of machine-learning component 172 is illustrated that may perform one or more machine-learning processes as described in this disclosure is illustrated. Machine-learning module may perform determinations, classification, and/or analysis steps, methods, processes, or the like as described in this disclosure using machine-learning processes. A machine-learning process includes any of the machine-learning processes as described above in more detail in reference to FIGS. 1-6. A machine-learning process uses training data 604 to generate an algorithm that will be performed by processor 148 and/or wearable device 104 to produce outputs 608 given data provided as inputs 612; this is in contrast to a non-machine-learning software program where the commands to be executed are determined in advance by a user and written in a programing language.

With continued reference to FIG. 6, training data 604 includes any of the training data as described above in more detail in reference to FIG. 1. For instance and without limitation, training data 604 may include a plurality of data entries, each entry representing a set of data elements that were recorded, received, and/or generated together; data elements may be correlated by shared existence in a given data entry, by proximity in a given data entry, or the like. Multiple data entries in training data 604 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations; correlations may indicate causative and/or predictive links between categories of data elements, which may be modeled as relationships such as mathematical relationships by machine-learning processes as described in further detail below. Training data 604 may be formatted and/or organized by categories of data elements, for instance by associating data elements with one or more descriptors corresponding to categories of data elements. As a non-limiting example, training data 604 may include data entered in standardized forms by persons or processes, such that entry of a given data element in a given field in a form may be mapped to one or more descriptors of categories. Elements in training data 604 may be linked to descriptors of categories by tags, tokens, or other data elements; for instance, and without limitation, training data 604 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 6, training data 604 may include one or more elements that are not categorized; that is, training data 604 may not be formatted or contain descriptors for some elements of data. Machine-learning algorithms and/or other processes may sort training data 604 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning component 172 may correlate any input data as described in this disclosure to any output data as described in this disclosure. As a non-limiting illustrative example, an input 612 may include a reproduction rate for a pathogen of possible contagion 164, and an output 608 may include a degree of transmission threat 152. In yet another non-limiting example, an input 612 may include one or more factors that may affect a reproduction rate 164, and an output may include a reproduction rate 164.

Further referring to FIG. 6, training data 604 may be filtered, sorted, and/or selected using one or more supervised and/or unsupervised machine-learning processes and/or models as described in further detail below; such models may include without limitation a training data classifier 616. Training data classifier 616 may include a "classifier," which as used in this disclosure is a machine-learning model as defined below, such as a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning component 172 may generate a classifier using a classification algorithm, defined as a process whereby a processor and/or any module and/or component operating thereon derives a classifier from training data 604. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data 604 to specific geographic locations where pathogens of possible contagion may be found and/or more likely to be found, demographic populations of users and/or currently proximate subjects, pathogens of possible contagion, and the like.

Still referring to FIG. 6, machine-learning component 172 may be configured to perform a lazy-learning process 620 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 6, machine-learning processes as described in this disclosure may be used to generate machine-learning models 624. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 624 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include at least a supervised machine-learning process 628. At least a supervised machine-learning process 628, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs 612 as described above as inputs, and outputs 608 as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 628 that may be used to determine relation between inputs and outputs. Supervised machine-learning processes may include classification algorithms as defined above. Scoring function may include calculating inoculation status, antibodies, security settings, sharing of systems that may be mapped to possible conditions based on prevalence in a local population and the like.

Further referring to FIG. 6, machine-learning processes may include at least an unsupervised machine-learning processes 632. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 6, machine-learning component 172 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naive B ayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes. Machine-learning algorithms and/or machine-learning processes may be updated in real-time to reflect and contain real time population statistics, outbreaks of pathogens of possible contagion 152, vaccination efficacy, mitigation efforts, and the like.

Figure 7A:
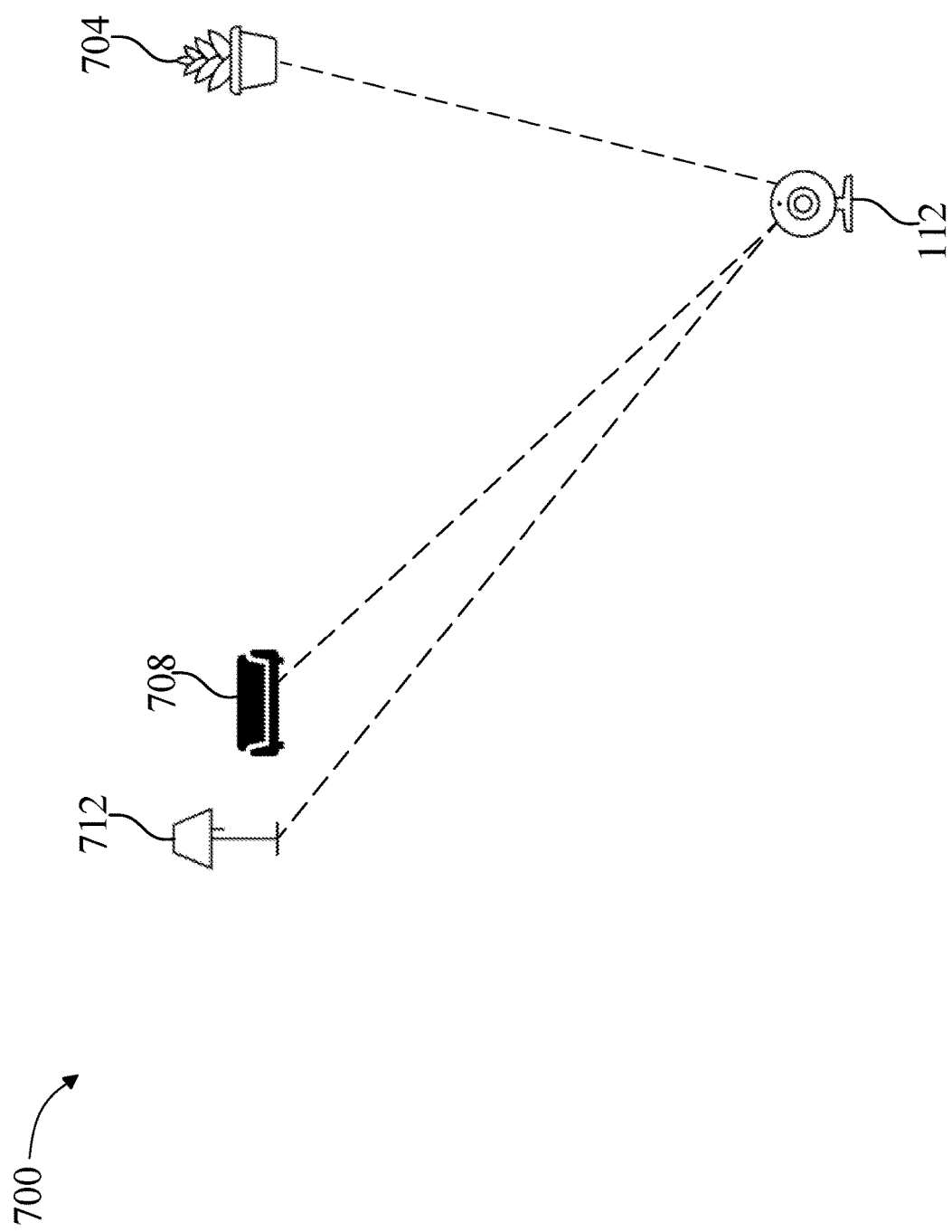
FIGS. 7A-B are diagrammatic representations of exemplary embodiments of detection component.
Figure 7B:
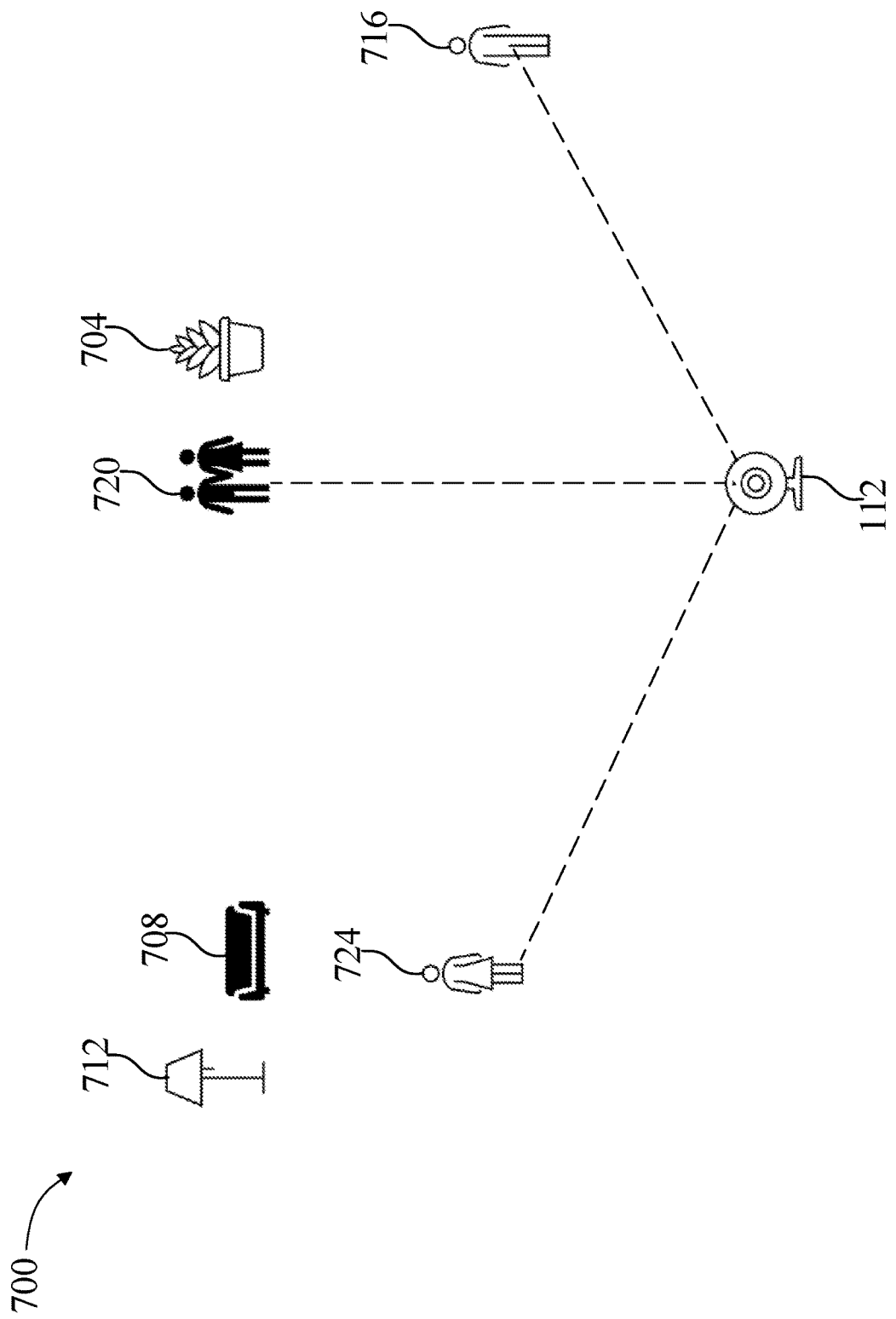

Referring now to FIGS. 7A-7B, exemplary embodiments 700 of detection component 112 are illustrated. Referring now to FIG. 7A, detection component 112 may include any component, device, and/or technology as described above in more detail in reference to FIG. 1. Detection component 112 may include a sensor 124, and/or a camera 128 as described above in more detail. Detection component 112 may be configured to detect baseline location measurement. A baseline location measurement includes any of the baseline location measurements as described above in more detail in reference to FIG. 1. For instance and without limitation, a baseline location measurement may detect any furniture, items, currently proximate subjects, landmarks, and the like that may be contained within a specified location, such as a particular room in a house or a public space such as an event stadium or movie theater. In an embodiment, a location may include an area that a user 108 is currently located, and/or an area that a user 108 may be located at in the future. For example, a baseline location measurement may be taken of an event hall where a user will be attending an event later on in the day. Information pertaining to a baseline location measurement may be stored and saved within wearable device 104. In an embodiment, a baseline location measurement may detect one or more landmarks contained within a location. For example, detection component 112 may detect a first landmark 704, such as a plant contained within a location, a second landmark 708 such as a couch, and a third landmark 712 such as a lamp located next to the couch. Wearable device 104 may utilize information pertaining to a landmark to offer suggestions to a user 108 about where the user may need to position themselves within a location to best protect the user's 108 health and risk of infection. For instance and without limitation, a landmark may convey transmission risk based on the material, composition, and/or ultraviolet exposure of a landmark. For example, the interior of a doorknob may have a different degree of threat as compared to the exterior of the doorknob. In yet another non-limiting example, a doorknob may have a first degree of threat during the day when the doorknob is located in direct sunlight, whereas the doorknob may have a second degree of threat during the evening and at night when the doorknob is not exposed to any sunlight or very low levels of sunlight. A landmark may also be used to aid in identifying protected locations in relation to a user 108. Referring now to FIG. 7B, detection component 112 may be utilized to detect one or more currently proximate subjects 116 that be present in a location and/or located near a user 108. In an embodiment, detection component 112 may detect a first currently proximate subject 716, a pair of second currently proximate subjects 720, and a third currently proximate subject 724. In an embodiment, wearable device 104 may calculate a degree of transmission threat 152 between the user 108 and each currently proximate subject, including a first degree of transmission threat 152 between the user 108 and the first currently proximate subject 716, a second degree of transmission threat 152 between the user 108 and the second currently proximate subject 720, and a third degree of transmission threat 152 between the user 108 and the third currently proximate subject 724. Wearable device 104 may calculate a degree of transmission threat 152 of a location where a user 108 is located, such as when there may be multiple currently proximate subjects 116 located in a particular location. For instance and without limitation, degree of transmission threat 152 of a location may reflect the overall threat level of a location for a user. For example, a location that has very poor air ventilation, few windows, and very little sunlight may have a higher degree of transmission threat to a user's health for transmitting pathogens of possible contagion, as compared to a location that has excellent air circulation, and plenty of windows and doors that can allow plenty of fresh air to be brought inside the location. In yet another non-limiting example, a location that is crowded but that has excellent air circulation and air conditioning may have a lower degree of transmission threat to a user's health for transmitting pathogens of possible contagion, as compared to a location that is not as crowded by that has very poor air circulation and outdated air filtration.

Figure 8C:
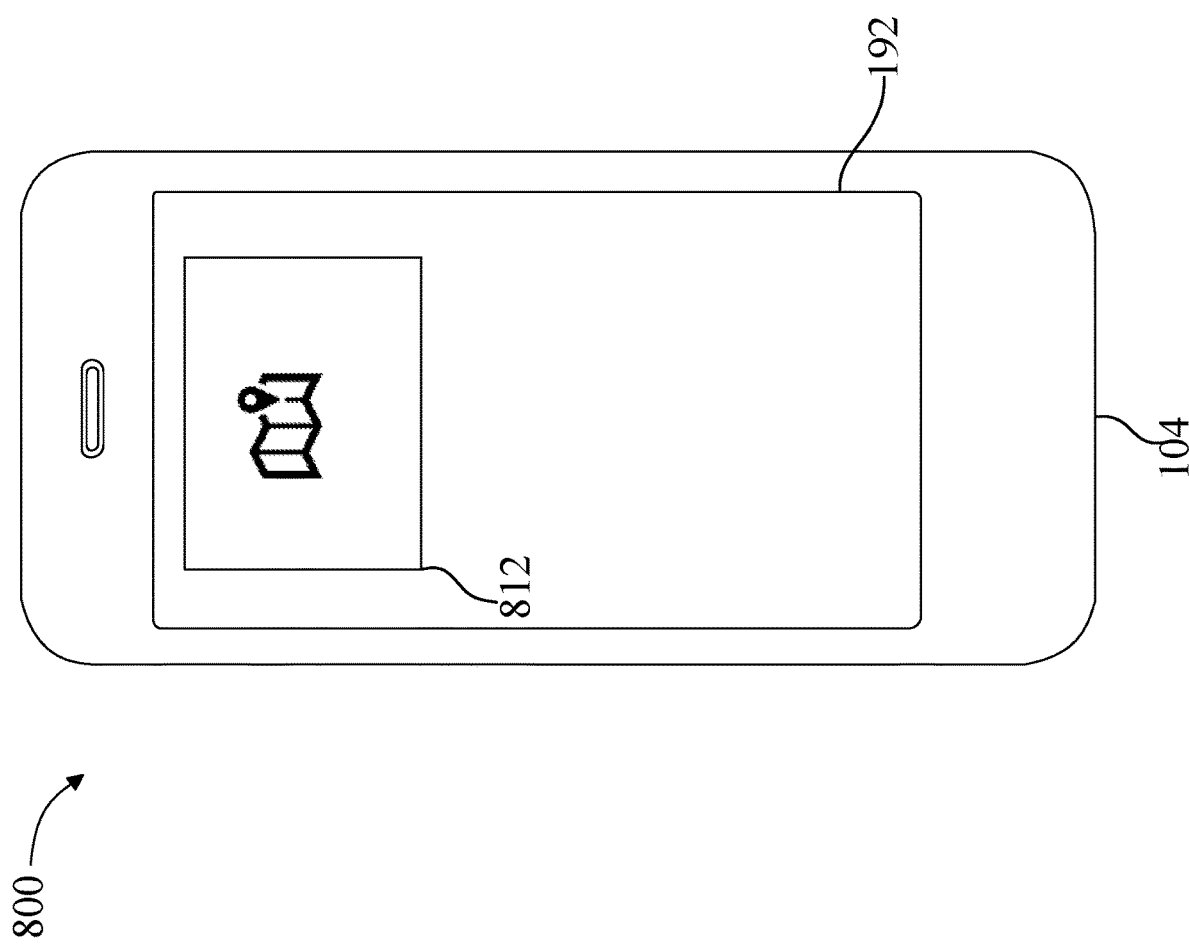

Referring now to FIGS. 8A-C, exemplary embodiments 800 of various outputs 184 are illustrated. Referring now to FIG. 8A, in an embodiment, wearable device 108 may display on graphical user interface 192, a degree of transmission threat 152, which may specify the degree of transmission threat of a location. A location may include any location as described above in more detail in reference to FIGS. 1-7. In an embodiment, an output 184 may include a visual display 804, which may visually provide information relating to a degree of transmission threat 152. For instance and without limitation, a visual display 804 may include an emoji, that may communicate if a location and/or currently proximate subject 116 is safe to be around or not. For example, a happy smiling face emoji may communicate to a user 108 that it is safe to stay in the location. An output 184 may include a tactile output, including any of the tactile outputs as described above in more detail in reference to FIG. 1. An output 184 may include one or more recommended mitigation components 188. For instance and without limitation, when a degree of transmission threat 152 of a location is 7%, wearable device 104 may display a mitigation component 188, recommending a user 108 to remain 6 feet away from all subjects contained within a location, to aid in reducing risk of transmission of a pathogen of possible contagion 156. In an embodiment, a mitigation component 188 may be selected and/or recommended for a user 108 as a function of a precipitating component relating to a pathogen of possible contagion 156. For instance and without limitation, a mitigation component 188 may recommend extra precautions to be taken such as wearing a mask and frequent handwashing if a precipitating component indicates that a pathogen of contagion such as rotavirus has been prevalent in certain demographics which a user 108 appears to fit into. Referring now to FIG. 8B, in an embodiment, wearable device 104 may display a degree of transmission threat 152 of a currently proximate subject 116. In an embodiment, an output 184 may include an emoji such as a sad face 808 when a currently proximate subject 116 and/or a location may not be safe for a user. In such an instance, a mitigation component 188 may recommend a user 108 to leave a location immediately, because the risk of danger, harm, and/or illness to a user 108 is too immense. In an embodiment, wearable device 104 may continue to generate outputs 184, including both visual and/or haptic outputs until a user has exited a location where there is a high degree of transmission threat 152 either to a currently proximate subject 116 and/or a location. For example, wearable device 104 may utilize location component 132 to sense and/or detect where a user 108 is located and continue to generate and transmit outputs 184 until a user 108 is no longer in danger. Referring now to FIG. 8C, in an embodiment, output 184 may identify a protected location in relation to a user 108. A protected location includes any of the protected locations as described above in more detail in reference to FIG. 1. In an embodiment, graphical user interface 192 may display a map 812, illustrating a route for a user 108 to travel to a protected location. For example, map 812 may display a photograph and/or image of location and show a visible route that a user should take to get to a protected location. This may include for example, avoiding currently proximate subjects 116, and/or navigating to and/or around landmarks, using information obtained from a baseline location measurement. In an embodiment, directions to a protected location may also be provided by tactile outputs, such as if wearable device 104 provides audio and spoken instructions for how a user 108 should travel to a protected location. In an embodiment, wearable device 104 may vibrate to provide instructions for how a user may seek to travel to a protected location.

Figure 9:
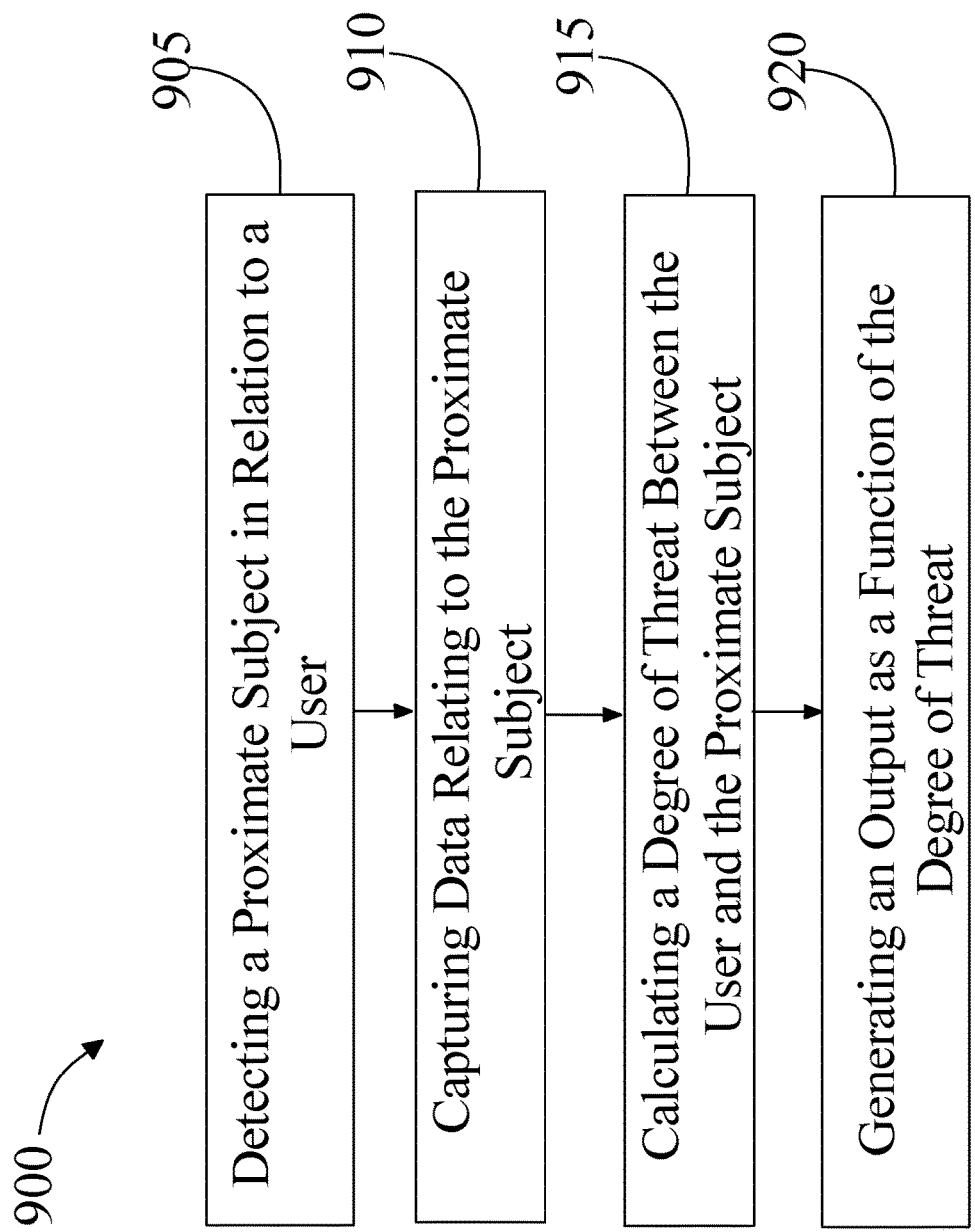
FIG. 9 is a process flow diagram illustrating an exemplary embodiment of a method of reducing exposure to pathogens of possible contagion.

Referring now to FIG. 9, an exemplary embodiment 900 of a method of reducing exposure to pathogens of possible contagion is illustrated. At step 905, a wearable device 104 detects a currently proximate subject 116 in relation to a user 108, wherein the user 108 is in possession of the wearable device 104. Wearable device 104 may include any of the wearable devices as described above in more detail in reference to FIGS. 1-8. In an embodiment, wearable device 104 detects a currently proximate subject 116 in relation to a user 108, using any of the methodologies as described above in more detail in reference to FIGS. 1-8. In an embodiment, were able device 104 may detect a currently proximate subject 116 using detection component 112, including for example sensor 124 and/or camera 128.

With continued reference to FIG. 9, at step 910, wearable device 104 captures data relating to a currently proximate subject 116. Data relating to a currently proximate subject 116 includes any of the data as described above in more detail in reference to FIGS. 1-8. Data may include information that may be publicly available about a currently proximate subject 116, including information such as if the currently proximate subject has a cough, has a temperature, has a rosy face, is perspiring heavily, has crackles or labored breathing, and the like. Data may include information that a currently proximate subject 116 may agree to share with wearable device 104, including an authenticator which may specify what information can be shared about a currently proximate subject 116 and the like with a user 108 and/or a wearable device. For instance and without limitation, a currently proximate subject 116 may agree to share information relating to the currently proximate subject's 116 immunization records but no other data.

With continued reference to FIG. 9, at step 915, wearable device 104 calculates a degree of transmission threat 152 between a user 108 and a currently proximate subject 116. A degree of transmission threat 152, includes any of the degrees of threat 152 as described above in more detail in reference to FIGS. 1-8. Wearable device 104 calculates a degree of transmission threat 152 by identifying a pathogen of possible contagion 156, locating a reproduction rate 164 for the pathogen of possible contagion 156, and calculating a degree of transmission threat 152 as a function of data relating to the currently proximate subject and the reproduction rate 164. This may be performed utilizing any of the methodologies as described above in more detail in reference to FIGS. 1-8.

With continued reference to FIG. 9, at step 920, wearable device 104 generates an output 184 as a function of a degree of transmission threat 152. An output 184 includes any of the outputs as described above in more detail in reference to FIGS. 1-8. An output 184 may include a message relating to a degree of transmission threat 152. For instance and without limitation, an output 184 may recommend a user to leave a location immediately, because a degree of transmission threat 152 is too high. In yet another non-limiting example, an output 184 may include a message informing a user 108 to avoid coming within more than 3 feet of a currently proximate subject 116. An output 184 may include a visual display, and/or a tactile output as described above in more detail in reference to FIGS. 1-8. An output 184 may identify a mitigation component that may aid in reducing a reproduction rate 164 of a pathogen of possible contagion 156. This may include any of the mitigation components as described above in more detail in reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
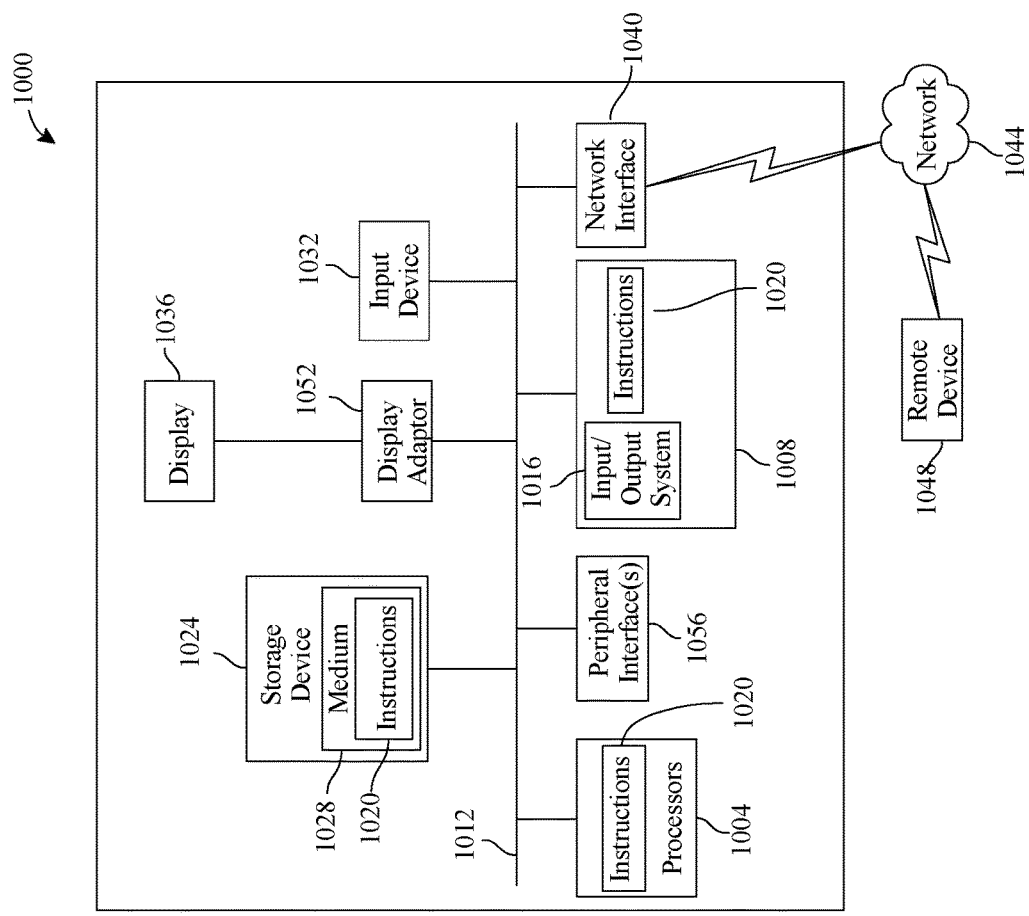
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A wearable device for reducing exposure to pathogens of possible contagion, the wearable device comprising:
   a detection component configured to:
      perform a baseline location measurement of a location containing a currently proximate subject;
      detect the currently proximate subject in relation to a user, wherein the user is in possession of the wearable device, and wherein the detection component is further configured to determine a distance from the currently proximate subject to the user by detecting a radio frequency wireless signal from an electronic device of the currently proximate subject and using signal strength of the detected radio frequency wireless signal to determine the distance;
   a data input component configured to capture data relating to the currently proximate subject, wherein:
      the data relating to the currently proximate subject further comprises an inoculation status of the currently proximate subject; and
      the inoculation status further comprises data indicating whether the currently proximate subject is opted in to reporting inoculation status;
   a processor configured to:
      calculate the degree of transmission threat between the user and the currently proximate subject, wherein calculating the degree of transmission threat further comprises:
         identifying a pathogen of possible contagion;
         locating a reproduction rate for the pathogen of possible contagion; and
         calculating the degree of transmission threat as a function of the data relating to the currently proximate subject and the reproduction rate; and
      determine a protected location within the location as a function of the degree of transmission threat and the baseline location measurement; and
   a user-signaling component configured to generate an output as a function of the degree of transmission threat, wherein the output includes an indication of the protected location.

2. The device of claim 1, wherein the detection component further comprises a sensor.

3. The device of claim 1, wherein the detection component further comprises a camera.

4. The device of claim 1, wherein:
   the processor is further configured to identify, using the baseline location measurement, a path within the location to the protected location; and
   the user-signaling component is further configured to display the path to the user.

5. The device of claim 1, wherein the detection component is further configured to detect the currently proximate subject in relation to a landmark.

6. The device of claim 1, wherein the detection component is further configured to detect a first currently proximate subject in relation to a second currently proximate subject.

7. The device of claim 1, wherein data relating to the currently proximate subject further comprises a physiological measurement.

8. The device of claim 1, wherein the data input component is further configured to:
   detect a signal from a device in the possession of the currently proximate subject;
   identify an authenticator of the currently proximate subject as a function of the signal; and
   capture data as a function of the authenticator of the currently proximate subject.

9. The device of claim 1, wherein locating the reproduction rate further comprises:
   retrieving a reproduction machine-learning model as a function of the identified pathogen of possible contagion; and
   outputting the reproduction rate as a function of the reproduction machine-learning model.

10. The device of claim 1, wherein calculating the degree of transmission threat further comprises:
    selecting a pathogen machine-learning model as a function of the pathogen of contagion;
    uploading the pathogen machine-learning model to the wearable device; and
    calculating the degree of transmission threat as a function of the uploaded pathogen machine-learning model.

11. The device of claim 1, wherein calculating the degree of transmission threat further comprises:
    retrieving an element of user data; and
    calculating the degree of transmission threat as a function of the user data.

12. The device of claim 1, wherein the processor is further configured to calculate a degree of transmission threat of a location wherein the user is located.

13. The device of claim 1, wherein the pathogen of possible contagion comprises a coronavirus.

14. The device of claim 1, wherein the processor is further configured to authenticate the identity of the user at timed intervals, while the user is in possession of the wearable device.

15. The device of claim 1, wherein the output further comprises a visual display.

16. The device of claim 1, wherein the output further comprises a tactile output.

17. The device of claim 1 further comprising:
identifying a precipitating component relating to the pathogen of possible contagion;
determining a mitigation component configured to reduce the reproduction rate; and
displaying the mitigation component.

18. A method of reducing exposure to pathogens of possible contagion, the method comprising:
performing, by a wearable device, a baseline location measurement of a location containing a currently proximate subject;
detecting by the wearable device, a currently proximate subject in relation to a user, wherein the user is in possession of the wearable device, and wherein the detection component is further configured to determine a distance from the currently proximate subject to the user by detecting a radio frequency wireless signal from an electronic device of the currently proximate subject and using signal strength of the detected radio frequency wireless signal to determine the distance;
capturing by the wearable device, data relating to the currently proximate subject, wherein:
the data relating to the currently proximate subject further comprises an inoculation status of the currently proximate subject; and
the inoculation status further comprises data indicating whether the currently proximate subject is opted in to reporting inoculation status;
calculating by the wearable device the degree of transmission threat between the user and the currently proximate subject, wherein calculating the degree of transmission threat further comprises:
identifying a pathogen of possible contagion;
locating a reproduction rate for the pathogen of possible contagion; and
calculating the degree of transmission threat as a function of the data relating to the currently proximate subject and the reproduction rate; and
determining a protected location within the location as a function of the degree of transmission threat and the baseline location measurement; and
generating by the wearable device, an output as a function of the degree of transmission threat, wherein the output includes an indication of the protected location.

* * * * *